United States Patent [19]
Dunbar

[11] Patent Number: 5,820,863
[45] Date of Patent: Oct. 13, 1998

[54] METHODS OF PREPARATION AND USE FOR ZONA PELLUCIDA ANTIGENS AND ANTIBODIES FOR STERILIZATION AND CONTRACEPTION

[75] Inventor: Bonita Sue Dunbar, Houston, Tex.

[73] Assignee: Zonagen, Inc., The Woodlands, Tex.

[21] Appl. No.: 396,452

[22] Filed: Feb. 28, 1995

Related U.S. Application Data

[63] Continuation of Ser. No. 55,831, Apr. 30, 1993, abandoned, which is a continuation of Ser. No. 899,112, Jun. 15, 1992, abandoned, which is a continuation of Ser. No. 625,208, Dec. 10, 1990, abandoned, which is a continuation of Ser. No. 106,087, Oct. 7, 1987, Pat. No. 4,996,297.

[51] Int. Cl.$^6$ .......................... A61K 38/16; A61K 39/00; C07K 14/705
[52] U.S. Cl. ................................ 424/185.1; 514/2; 514/8; 514/12; 530/395; 530/350; 530/850; 530/853
[58] Field of Search .................................... 530/395, 350, 530/850, 853; 514/2, 8, 12, 21; 424/185.1, 184.1; 435/69.1, 69.7

[56] References Cited

U.S. PATENT DOCUMENTS

| | | | |
|---|---|---|---|
| 3,992,520 | 11/1976 | Gwatkin | 424/85.9 |
| 4,526,716 | 7/1985 | Stevens | 530/403 |
| 4,792,520 | 12/1988 | Stambrook | 435/6 |
| 4,795,634 | 1/1989 | Grimes | 424/85.9 |
| 4,996,297 | 2/1991 | Dunbar | 530/395 |
| 5,348,866 | 6/1994 | Isojima | 439/69.3 |

FOREIGN PATENT DOCUMENTS

| | | |
|---|---|---|
| 3028889 | 9/1984 | European Pat. Off. |
| 1103778 | 2/1987 | European Pat. Off. |
| 1103786 | 3/1987 | European Pat. Off. |
| WO87/05516 | 3/1987 | WIPO |

OTHER PUBLICATIONS

Aitken, et al., *J. Reprod. Fert.* 62:597–606, 1981).
Aitken, et al., *Gamte Research* 4:41–47 (1981).
Aitken, et al., In *Immunological Aspects of Reproduction and Fertility Control* (Hearn, ed.) MTP Press Ltd., pp. 173–201 (1980).
Bamezai et al., *Journal of Bio Sciences* 7(2):105–113 (1985).
Bliel et al., *Cell*, 20:873–882 (1980).
Dean et al., *Adv. Exp. Med. Biol.* 207:37–53 (1986).
Dietl, *Experimentia*, 38:502–503 (1982).
Dietl et al., Abstract of Am. J. Reprod. Immunol. 4(3) 116–121 (1983).
Dietl et al., Hoppes–Seylers Z. Physiol., 363:381–386 (1982).
Drell et al., *Biology of Reproduction* 30:435–444 (1984).
Drell et al., *Biology of Reproduction* 30:445–457 (1984).
Dunbar et al., *Biochem* 19:356–365 (1980).
Dunbar, et al., *Chemical Abstracts*, 95:58740μ, 1981.
Dunbar, *Proceedings of the International Conference on Reproductive Immunology* (Gill and Wegmann, eds.) Oxford University Press, England, pp. 505–535 (1982).
East et al., *The Journal of Cell Biology*, 98:795–800, 1984.
East et al., *Developmental Biology* 109:268–273 (1985).
Glass et al., *Fertility and Sterility* 25:484–493 (1974).
Greve, et al., *Cell*, 31:749–759 (1982).
Gupta et al., *Biol. Abs.*, 82(4), ab 37905 (Aug. 1986).
Gwatkin, *J. Reprod. Fertil.* 7:99–105 (1964).
Gwatkin et al., *Fertility and Sterility* 28(8):871–876 (1977).
Gwatkin et al., *Gamete Research* 1:19–26 (1978).
Hedrick, et al., *Analytical Biochemistry* 157:63–70 (1986).
Hedrick, et al., *Developmental Biology* 121:478–488 (1987).
Isojima et al., *Acta Obst. Gynaec. Jpn.* 33(11):1995–1996 (1981).
Isojima et al., *Journal of Reproductive Immunology* 6:77–87 (1984).
Isomjima et al., In *Immunological Approaches to Contraception and Promotion of Fertility*, 323–333 (1986).
Koyama et al., *Journal of Reproductive Immunology* 7:187–198 (1985).
Mahi et al., *The Journal of Experimental Zoology* 210(1):129–135 (1979).
Mahi–Brown et al., *The Journal of Experimental Zoology*, 222:89–95 (1982).
Mori et al., *Journal of Reproductive Immunology* 8:337–345 (1985).
Mori et al., *Journal of Reproductive Immunology* 8:1–11 (1985).
Ringuette et al., *PNAS*, 85:4341–4345, 1986.
Sacco et al., *Fertility and Sterility* 31:503–506 (1979).
Sacco, *J. Reprod. Fert.* 56:533–537 (1979).
Sacco et al., *Fertility and Sterility* 39(3):350–357 (1983).
Shivers, In *Immun. Influence on Human Fertility*, Proc. of workshop on fertility in human reproduction (Boettcher, ed.) Academic Press, pp. 13–23 (1977).
Shivers et al., In *Immunological Aspects of Infertility and Fertility Regulation* (Dhindsa/Schumacher, eds.), Elsevier North Holland, Inc., pp. 173–182 (1980).
Shivers et al., *J. Med. Primatol* 7:242–248 (1978).
Shivers et al., *Science* 178:1211–1213 (1972).
Tsunoda et al., *JARO* 15(3):191–195 (1982).
Yurewicz et al., *The Journal of Biological Chemistry*, 262:564–571, 1987.

*Primary Examiner*—Robert A. Wax
*Assistant Examiner*—G. E. Bugaisky
*Attorney, Agent, or Firm*—Marshall, O'Toole, Gerstein, Murray & Borun

[57] ABSTRACT

The invention relates to antigenic preparations useful for inducing the production of antibodies in an individual which will bind to epitopes on zona pellucida. Also disclosed are immunogenic compositions and methods for immunizing an individual to enable the production of antibodies to zona pellucida antigens. Also disclosed are the use of these recombinant molecules and monoclonal antibodies thereto for immunocontraception or sterilization.

10 Claims, 9 Drawing Sheets

FIG. 2

N-TERMINAL AMINO ACID SEQUENCES OF RABBIT ZP GLYCOPROTEINS

I(E)  Lys-Gln-Pro-Lys-Thr-Asp-Pro-Gly-Val-Leu-His-X-Arg-Pro-Trp-Asn-Phe-Lys-Phe-Thr-Ile-

II(E) Lys-Gln-Leu-Gln-Pro-Ser-Asp-Pro-Ala-Phe-Pro-Gly-Thr-Val-His-X-Asn-Glu-

III(E) N-blocked

E: Deglycosylated with endo beta-galactosidase
X: Amino acid residue undetermined

N-TERMINAL AMINO ACID SEQUENCES OF PIG ZP GLYCOPROTEINS

I(E)  X-Val-Pro-Thr-Ile-Gly-Leu-Cys-Asp-Ala-Val-Pro-Val-Trp*-Asp-Arg-Leu-Pro-Cys-Ala-Pro-
      Leu Arg

I(T)  X-Val-Pro-Thr-Ile-Gly-Leu-Cys-Asp-Ala-Val--Pro-Val-Ser*-Asp-Arg-Leu-Pro-Gln-Ala-Pro-Pro-Pro*-Asp-
      Leu Arg                                                                              Thr

II(E) X-X-Asn-Val-Lys*-Arg-Glu-Asp-Ser*-X-Gln-Arg-Met*-Gly-Gly-Ser-

III(E) X-X-Pro-Gln-Leu-Val-Asn-Thr-Ala-Phe-Pro-X-Ile*-Val*-

E: Deglycosylated with endo beta-galactosidase
T: Deglycosylated with trifluoromethane sulfonic acid
X: Amino acid residue undetermined
*: Amino acid residue identification tentative

```
  1  TAGGAGACCA CATCTTTTA GATACACTTC CTGCTTGCTT TCTGTTAGAG GTAGCTACTT
 61  CACCTACAGG GTCTCCTTGC AAATTATTT GTCTCCTTGC CTTCCACAGA TTTCTGAGGA CTTGTATGAC
121  TGAGGCAAGT GGAGATGCT AGTGAATGAA TGCTATTGT TTCAATATT GATGAAGCAA
181  TGCATCCATC ACTTTTTAAT TTCATTAGTA GGTCTCTCA ATTTGTCTC CTGATTTCTA
241  CATTCTGAGT TCACAAGATC AAGGATCATC TGTACACAAG TACCGTGTAT GTTAGTGATG
301  TGTCACACAC AGA
  1  ATGGGACAAA GCCCAGAAGA GAGGGGTGAA GCTTGTTTCT GTTCTCTGGG TGGAGAAATG
 61  CAGGACAGCT GGAGCACACA TTGGATGAGT CATTATTCCC TGCAGCCAAT ACCAGTGAGC
121  ACTTACCAAG TCTGATTAAG AAAAGCGCA AGTGTATGCA GCCCAAAGAT TTTTTCCCA
181  AAACACCAGA TAATGATAAA AGACTTCAA AGAAATTTGA CAAAATGGCT CAAGAACTAC
241  AGAGGCAAAA AACCACTCTA GATAATGATA CGCCTGTTCT CTTATTTGAT CTAATGATAT
301  GTTGACGTTA TAGTCCCACA GTTAAGTGTG TAGTCACACA GCTCATGAAG GA
```

P2

```
  1  AGAATGACAG TGCAGTGCTA TTACACCAGA GATGACATGC TACTCAATGC CAATATCAAA
 61  AGTCTTCCTC CTCCTGTGCA CTCAGTGAAG CCAGGTCCAC TTGCTTTGAG CCTGCAAACC
121  TACCCAGATG AGTCCTATCA ACAGCCTTAC AGGGTCAATG AGTACCCTAT AGTGAAATAC
181  CTCCGCCAAC CAATTTACAT GGAAGTGAGA GTCCTAAATA GAAATGACCC CAATATCAAG
241  CTGGCCCTAG ATGACTGCTG GCAACATGTG TCCATGGACC CAGCATCTCT CCCAAGTGGA
301  GTATTGTCAT GGACGGCTGT GAGTATAGCC TGGACAACTA TCAAACTAAC TTCACCCAGT
361  TGGCTCCTCT GTGACCTATC CTGAGCACTA CCAGAGGTTT GATGTGAAGA CCTTTGCCTT
421  TGTATCAGAG GCCCAAGCAC GCTCTAGCCT GGTCTATCCT CCACTGCAGT GCCTTAATCT
481  GCAATCAACA CTATCCTGAC TCTCCTTTGT GCTCGTGTGAC TTGCCCTGGG TCATCTAGAC
541  ACAGGCGAGC CACAGGGAAC ACCGAAGAGG AGAGAGTGAC AGCCAGCCTC CCAGGACCCA
601  TTTCCTGTT ACCGAATGGC TCTTCCTTCA GAGGTGTTGG GGATTCCAAG AGCCAGTGGA
661  TGGCTGGAGA TGTTACTTCT AAACAATGG CTGCTGTGGC TGCCGTAGCA GACCATGGGA
721  CAACTCTAGG CTTCATCAGT TACCTGTGTA AAAGAGGAC GGTGTACTGG AGCATGGGAC
781  TTGACTTGCA AATAAAATGG TTGAAATAAA AAAAAAACC CATGATGTTA AGTCACTAAC
     C
```

```
                                              P3
   1 GTTTTTTTT TTGCCAACGA TGGCTCCTGG TAGCACCATG TGGCTGTTAG GGTACATCTT
  61 TCTCTGTTTC CCTGTATCAT TTGCTCTGAT CAAGCAACCT CTTTAAGTGA CTCCTACTGA
 121 TCCTGGTGTG CTCCACTGTA GACCATGGAA CTTTAAGTTT ACTATAAATT TTCAGAACCA
 181 GGAGACAGGG TCTTCCCCTG TACTTGTAAC CTGGACAAC CAAGGGCGAT TGCACAGGCT
 241 GCAGAATGAC ACTGACTGTG GCACCCGGGT AGGAGAGGGT CCAGGCCCCT CCGTGGTACT
 301 GGAAGCAAAC TACAGCAGCT GCTACGTCAC TGAGTCGGAA CCGTACTACG TCATGCTGGT
 361 CGGGGTGAA GAGGTGGACG CAGCAGACA AAACCTGGTT ACAAAGCAGC AGTGCTTAA
 421 GTGTCCGATG CATCTCCCAG CTCCAGATGC TGGACTGTGC GACTCTGTCC CAGTGCAGGA
 481 CAGGCTGCCC TGTGTCTACTG CACCCATCTC ACAAGAAGAC TGTGAGGAAC TAGGTTGCTG
 541 CCACAGCTCC GAAGAGTAA ATGCCTGTTA CTATGGAAAC ACAGTGACCT CACACTTGGT
 601 ACCCAAGAGG GCCACTTCTC CATCGCCGTG TCCCGGAATG TGTCCTCGCC CCCACTGCAC
 661 TTGGATTCTG TGCACCTGGT CTTCGGGAAT GACAGTGAAT GCCAGCCTGT GGTAGCAACG
 721 CGTGCCTTTG TCCTGTTTCT GTTCCCATTT ACTGCCTGTG GTACCACAAG ACAGATCACT
 781 GGAGATAGAG CAATATATGA AAATGAGCTG CTTGCCACTA GGGAAGTGAG AACTTGGAGC
 841 CGTGGTTCTA TCACCCGTGA CAGCATCTTC AGGCTCCGGG TCAGCTGCAG CTACTCCATA
 901 AGCAGCAGTG CTCTCCCAGT TGATATGCAT GTGTTGACTC TTCCACCACC ACTTCCGGAG
 961 ACCCAGCCTG GGCCCCCTCAC TGTGGTACTT CAGATTGCTA AAGATAAAGA CTACCACTCT
1021 TACTACACCA TGGATGACTA CCCAGTGGTA AAGTTACTTC GGGATCCCAT CTACTGGATG
1081 TTTCCATCCT TTACAGGACA GATCCATACC TAGGTCTACG CCTGCATCAG TGTTGGGCCA
1141 CACCAAGGAC GAACCCCTTG TATCAACCAC AGTGGCCCAT ACTGGTGAAG GGATGCCCTT
1201 ACACTGGAGA CAACTATCAA ACCCAGTCCA TCCCAGTCCA GGAAGCCTTC GATCTGCCAT
1261 TCCCCTCTCA CCACCAGCGC TTCAGCATTT CCACCTTCAG CTTTCTGGAT TCCTCAGTTG
1321 CAAAGGAGGC TCTAAAGGA CCGATATATC TGCACTGCAG TGTGTCAGTC TGCAAGCCTA
1381 CTGGGACACA ATCCTGTACG GTAACCTGTC CTATTGACAG TCGAAGAAGA AACTCGGACA
1441 TCAATTCCA GCTAACACT GCTAACATTT CTAGCAAGGG ACCCATGATT CTACTTCAG
1501 CCACAGAGGA TCCCTCAGAA AAGCTCCATA AACACTCAGG TGTTCCTGTG CATCCTGGAG
1561 CTCTATGGGT GGCAGGCCTT TCTGGGATCT TCATCATTGG AGCCTTGCTT GTATCCTATG
1621 TGGCAATCAG GACACGAAGA TGAGTTCCTT GGGCCAAATA TATCAATAAA ACCAGAGTGC
1681 ACCACCAAAA AAAAAAAAA AAAC

FIG. 4b
```

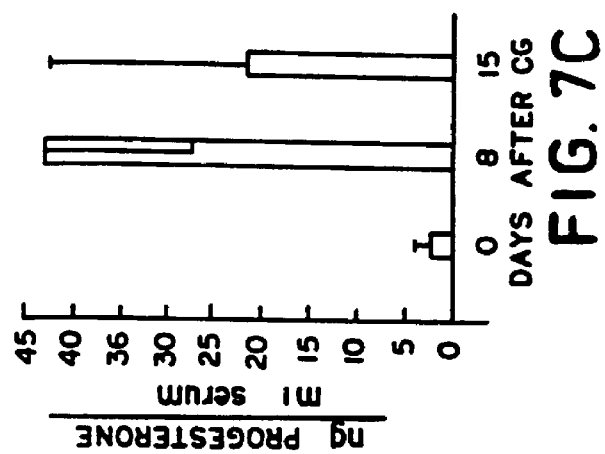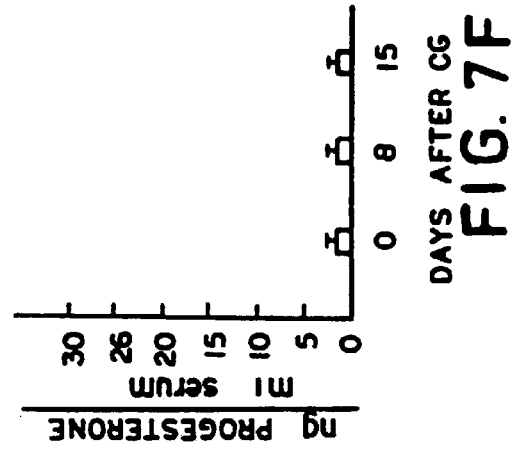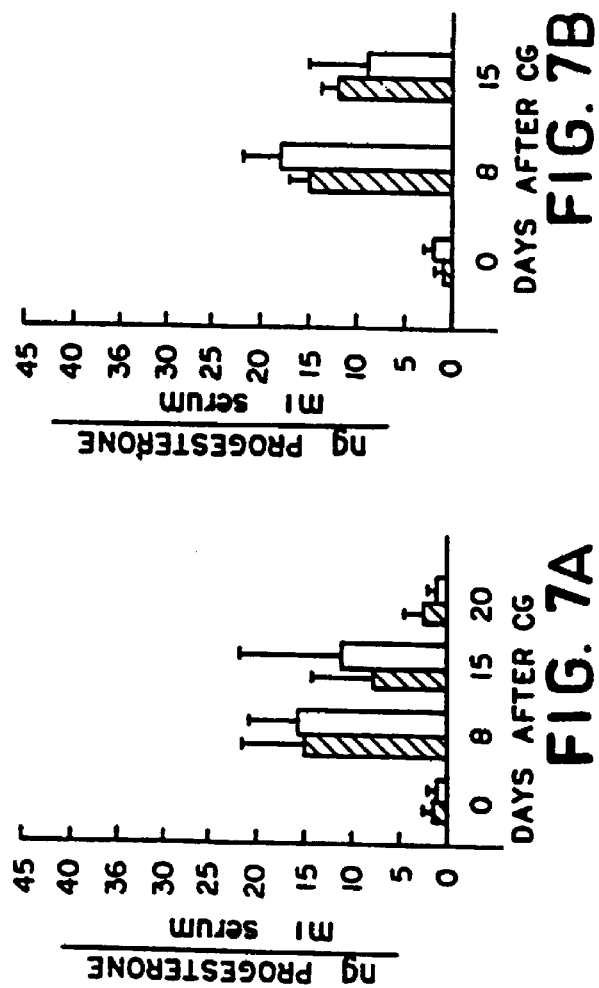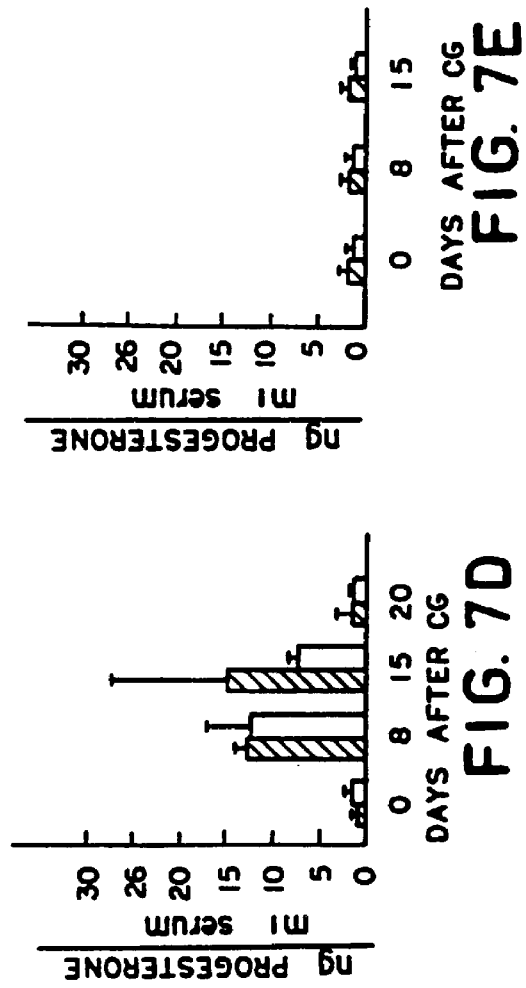

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 313 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TAGGAGACCA   CATCTTTTTA   GATACACTTC   CTGCTTGCTT   TCTGTTAGAG   GTAGCTACTT        60

CACCTACAGG   GTCTCCTTGC   AAATTTATTT   CTTCCACAGA   TTTCTGAGGA   CTTGTATGAC       120

TGAGGCAAGT   GGAGGATGCT   AGTGAATGAA   TGCTATTTGT   TTTCAATATT   GATGAAGCAA       180

TGCATCCATC   ACTTTTTAAT   TTCATTAGTA   GGTTCTCTCA   ATTTGTCTC    CTGATTTCTA       240
```

```
CATTCTGAGT  TCACAAGATC  AAGGATCATC  TGTACACAAG  TACCGTGTAT  GTTAGTGATG    300

TGTCACACAC  AGA                                                          313
```

( 2 ) INFORMATION FOR SEQ ID NO:2:

( i ) SEQUENCE CHARACTERISTICS:
        ( A ) LENGTH: 352 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ATGGACAAA   GCCCAGAAGA  GAGGGGTGAA  GCTTGTTTCT  GTTCTCTGGG  TGGAGAAATG     60

CAGGACAGCT  GGAGCACACA  TTGGATGAGT  CATTATTCCC  TGCAGCCAAT  ACCAGTGAGC    120

ACTTACCAAG  TCTGATTAAG  AAAAAGCGCA  AGTGTATGCA  GCCCAAAGAT  TTTTTCCCA     180

AAACACCAGA  TAATGATAAA  AGACTTCAAA  AGAAATTTGA  CAAAATGGCT  CAAGAACTAC    240

AGAGGCAAAA  AACCACTCTA  GATAATGATA  CGCCTGTTCT  CTTATTTGAT  CTAATGATAT    300

GTTGACGTTA  TAGTCCCACA  GTTAAGTGTG  TAGTCACACA  GCTCATGGAG  GA            352
```

( 2 ) INFORMATION FOR SEQ ID NO:3:

( i ) SEQUENCE CHARACTERISTICS:
        ( A ) LENGTH: 821 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
AGAATGACAG  TGCAGTGCTA  TTACACCAGA  GATGACATGC  TACTCAATGC  CAATATCAAA     60

AGTCTTCCTC  CTCCTGTGGC  CTCAGTGAAG  CCAGGTCCAC  TTGCTTTGAG  CCTGCAAACC    120

TACCCAGATG  AGTCCTATCA  ACAGCCTTAC  AGGGTCAATG  AGTACCCTAT  AGTGAAATAC    180

CTCCGCCAAC  CAATTTACAT  GGAAGTGAGA  GTCCTAAATA  GAAATGACCC  CAATATCAAG    240

CTGGCCCTAG  ATGACTGCTG  GGCAACATCT  TCCATGGACC  CAGCATCTCT  CCCAAGTGGA    300

GTATTGTCAT  GGACGGCTGT  GAGTATAGCC  TGGACAACTA  TCAAACTAAC  TTCACCCAGT    360

TGGCTCCTCT  GTGACCTATC  CTGAGCACTA  CCAGAGGTTT  GATGTGAAGA  CCTTTGCCTT    420

TGTATCAGAG  GCCCAAGCAC  GCTCTAGCCT  GGTCTATCTT  CCACTGCAGT  GCCTTAATCT    480

GCAATCAACA  CTATCCTGAC  TCTCCTTTGT  GCTCTGTGAC  TTGCCCTGGG  TCATCTAGAC    540

ACAGGCGAGC  CACAGGGAAC  ACCGAAGAGG  AGAGAGTGAC  AGCCAGCCTC  CCAGGACCCA    600

TTCTCCTGTT  ACCGAATGGC  TCTTCCTTCA  GAGGTGTTGG  GGATTCCAAG  GAGCATGGGA    660

TGGCTGGAGA  TGTTACTTCT  AAAACAATGG  CTGCTGTGGC  TGCCGTAGCA  GGTGTACTGG    720

CAACTCTAGG  CTTCATCAGT  TACCTGTGTA  AAAAGAGGAC  CATGATGTTA  AGTCACTAAC    780

TTGACTTGCA  AATAAAATGG  TTGAAATAAA  AAAAAAACC   C                         821
```

( 2 ) INFORMATION FOR SEQ ID NO:4:

( i ) SEQUENCE CHARACTERISTICS:
        ( A ) LENGTH: 1705 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:4:

| | | | | | | |
|---|---|---|---|---|---|---|
| GTTTTTTTTT | TTGCCAACGA | TGGCTCCTGG | TAGCACCATG | TGGCTGTTAG | GGTACATCTT | 60 |
| TCTCTGTTTC | CCTGTATCAT | TTGCTCTGAT | CAAGCAACCT | AAGCCTGAGA | CTCCTACTGA | 120 |
| TCCTGGTGTG | CTCCACTGTA | GACCATGGAA | CTTTAAGTTT | ACTATAAATT | TTCAGAACCA | 180 |
| GGAGACAGGG | TCTTCCCCTG | TACTTGTAAC | CTGGGACAAC | CAAGGGCGAT | TGCACAGGCT | 240 |
| GCAGAATGAC | ACTGACTGTG | GCACCCGGGT | AGGAGAGGGT | CCAGGCCCCT | CCGTGGTACT | 300 |
| GGAAGCAAAC | TACAGCAGCT | GCTACGTCAC | TGAGTCGGAA | CCGTACTACG | TCATGCTGGT | 360 |
| CGGGGTTGAA | GAGGTGGACG | CAGCTGGACA | AAACCTGGTT | ACAAAGCAGC | AGCTGCTTAA | 420 |
| GTGTCCGATG | CATCTCCCAG | CTCCAGATGC | TGGACTGTGC | GACTCTGTCC | CAGTGCAGGA | 480 |
| CAGGCTGCCC | TGTGCTACTG | CACCCATCTC | ACAAGAAGAC | TGTGAGGAAC | TAGGTTGCTG | 540 |
| CCACAGCTCC | GAAGAGGTAA | ATGCCTGTTA | CTATGGAAAC | ACAGTGACCT | CACACTTGGT | 600 |
| ACCCAAGAGG | GCCACTTCTC | CATCGCCGTG | TCCCGGAATG | TGTCCTCGCC | CCCACTGCAC | 660 |
| TTGGATTCTG | TGCACCTGGT | CTTCGGGAAT | GACAGTGAAT | GCCAGCCTGT | GGTAGCAACG | 720 |
| CGTGCCTTTG | TCCTGTTTCT | GTTCCCATTT | ACTGCCTGTG | GTACCACAAG | ACAGATCACT | 780 |
| GGAGATAGAG | CAATATATGA | AAATGAGCTG | CTTGCCACTA | GGGAAGTGAG | AACTTGGAGC | 840 |
| CGTGGTTCTA | TCACCCGTGA | CAGCATCTTC | AGGCTCCGGG | TCAGCTGCAG | CTACTCCATA | 900 |
| AGCAGCAGTG | CTCTCCCAGT | TGATATGCAT | GTGTTGACTC | TTCCACCACC | ACTTCCGGAG | 960 |
| ACCCAGCCTG | GGCCCCTCAC | TGTGGTACTT | CAGATTGCTA | AGATAAAGA | CTACCACTCT | 1020 |
| TACTACACCA | TGGATGACTA | CCCAGTGGTA | AAGTTACTTC | GGGATCCCAT | CTACTGGATG | 1080 |
| TTTCCATCCT | TTACAGGACA | GATCCATACC | TAGGTCTACG | CCTGCATCAG | TGTTGGGCCA | 1140 |
| CACCAAGGAC | GAACCCCTTG | TATCAACCAC | AGTGGCCCAT | ACTGGTGAAG | GGATGCCCTT | 1200 |
| ACACTGGAGA | CAACTATCAA | ACCCAGCTAA | TCCCAGTCCA | GGAAGCCTTC | GATCTGCCAT | 1260 |
| TCCCCTCTCA | CCACCAGCGC | TTCAGCATTT | CCACCTTCAG | CTTTCTGGAT | TCCTCAGTGG | 1320 |
| CAAAGGAGGC | TCTAAAAGGA | CCGATATATC | TGCACTGCAG | TGTGTCAGTC | TGCCAGCCTA | 1380 |
| CTGGGACACA | ATCCTGTACG | GTAACCTGTC | CTATTGACAG | TCGAAGAAGA | AACTCGGACA | 1440 |
| TCAATTTCCA | GAACAGTACT | GCTAACATTT | CTAGCAAGGG | ACCCATGATT | CTACTTCAAG | 1500 |
| CCACAGAGGA | TCCCTCAGAA | AAGCTCCATA | AACACTCAGG | TGTTCCTGTG | CATCCTGGAG | 1560 |
| CTCTATGGGT | GGCAGGCCTT | TCTGGGATCT | TCATCATTGG | AGCCTTGCTT | GTATCCTATG | 1620 |
| TGGCAATCAG | GACACGAAGA | TGAGTTCCTT | GGGCCAAATA | TATCAATAAA | ACCAGAGTGC | 1680 |
| ACCACCAAAA | AAAAAAAAAA | AAAAC | | | | 1705 |

(2) INFORMATION FOR SEQ ID NO:5:

(i) SEQUENCE CHARACTERISTICS:
(A) LENGTH: 25 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:5:

Lys Gln Pro Lys Pro Glu Thr Pro Thr Asp Pro Gly Val Leu His Xaa
 1               5                  10                  15
Arg Pro Trp Asn Phe Lys Phe Thr Ile
            20                  25

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

```
Lys Gln Leu Gln Pro Ser Asp Pro Ala Phe Pro Gly Thr Val His Xaa
 1               5                  10                  15
Asn Glu
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

```
Xaa Val Pro Thr Ile Gly Leu Cys Asp Ala Val Pro Val Trp Asp Arg
 1               5                  10                  15
Leu Pro Cys Ala Pro
             20
```

( 2 ) INFORMATION FOR SEQ ID NO:8:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

```
Xaa Val Pro Thr Ile Gly Leu Cys Asp Ala Val Pro Val Ser Asp Arg
 1               5                  10                  15
Leu Pro Gln Ala Pro Pro Pro Asp
             20
```

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

```
Xaa Xaa Asn Val Lys Arg Glu Asp Ser Xaa Gln Arg Met Gly Gly Ser
 1               5                  10                  15
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS:

(D) TOPOLOGY: linear (ii) MOLECULE TYPE: peptide (xi) SEQUENCE DESCRIPTION: SEQ ID NO:10:

```
Xaa Xaa Pro Gln Leu Val Asn Thr Ala Phe Pro Xaa Ile Val
1               5                   10
```

METHODS OF PREPARATION AND USE FOR ZONA PELLUCIDA ANTIGENS AND ANTIBODIES FOR STERILIZATION AND CONTRACEPTION

This is a Continuation of U.S. application Ser. No. 08/055,831, filed Apr. 30, 1993, now abandoned, which is was a continuation of U.S. application Ser. No. 07/899,112, filed Jun. 15, 1992, now abandoned, which was a continuation of U.S. application Ser. No. 07/625,208, filed Dec. 10, 1990, now abandoned, which was a continuation of U.S. application Ser. No. 07/106,087, filed Oct. 7, 1987, which issued on Feb. 26, 1991 as U.S. Pat. No. 4,996,297.

BACKGROUND OF THE INVENTION

1. Field of the Invention

The present invention relates to the preparation and use of zona pellucida (ZP) antigens and monoclonal antibodies for contraception or sterilization in individuals. The present invention also relates to immunological contraception. More specifically, the present invention relates to immunological contraception utilizing zona pellucida antigens produced by recombinant DNA technology to actively immunize an individual against pregnancy, or monoclonal antibodies prepared against the zona pellucida antigens to passively immunize the individual. In addition, the present invention relates to the use of anti-idiotypic monoclonal antibodies which would mimic ZP antigens to actively immunize an individual against pregnancy.

This invention also relates to monoclonal anti-zona pellucida antibody, to novel hybridoma cells which express such antibody, and to a method for producing such hybrid cells and anti-zona pellucida antibody.

2. Brief Description of the Background Art

The zona pellucida is the complex extracellular glycoprotein matrix which surrounds the mammalian oocyte. This matrix is formed during the early stages of oocyte growth and follicular cell differentiation and serves to protect the oocyte and embryo until implantation in the uterine wall (Austin, et al., *Reproduction in Mammals: Germ Cells and Fertilization*, Cambridge Univ. Press, Cambridge, England (1982)). In addition, the zona pellucida plays an important role in the fertilization process since the sperm must first adhere to and penetrate the zona pellucida. After binding to the zona pellucida of an oocyte, the sperm must penetrate the zona pellucida. Sperm penetration of the zona pellucida is probably mediated by the limited hydrolysis of zona pellucida components by sperm enzymes such as acrosin (McRorie et al., *Ann. Rev. Biochem.* 43: 777 (1974); Dunbar et al., *Biol. Reprod.* 32:619 (1985), and Stambaugh, *Gam. Res.* 1:65, 1978). The zona pellucida remains intact after fertilization, to ensure proper embryonic development and perhaps to prevent embryo fusion in the oviduct (Mintz, *Science* 138:594, 1962).

Finally, the zona pellucida plays a role in the block to polyspermy. In some mammalian species, fertilization alters sperm binding to the zona and its resistance to proteolytic digestion (Austin and Braden, *J. Exp. Biol.* 33:358, 1956).

There are major biological, morphological, physiological and immunochemical variations in properties among the zona pellucida of rodents as compared with the zona pellucida of other species including sub-human primates and humans. See reviews by Dunbar, In *Mechanism and Control of Fertilization* (J. Hartmann, ed.), Academic Press, New York, pp. 139 (1983); Dunbar, In *International Congress on Reproductive Immunology* (Wegmann and Gill III, eds.), Oxford Univ. Press, London, pp. 505 (1983) and Dunbar et al., In: *Modern Cell Biology* 3, (Satir, ed.) Alan R. Liss, New York, pp. 77 (1984). Although mammalian zona pellucida is composed of a limited number of major glycoproteins (Bleil et al., *Dev. Biol.* 76:185 (1980); Dunbar et al., *Biol. Reprod.* 24:1111 (1981); Timmons and Dunbar, *Biol. Reprod.* (1987)), the structural and functional relationships of zona pellucida proteins of different species vary.

Attempts to develop an effective and economical method of immunocontraception have been hindered by the lack of sufficient material to produce quantities of antigen or antibodies needed to produce a vaccine which would either inhibit fertilization of the oocyte by the sperm, prevent implantation of a fertilized egg, or prevent the development of the ovaries thereby making the animal permanently sterile. Early attempts to develop immunocontraceptive methods have not been very successful. These attempts have included the use of naturally occurring circulating peptide hormones such as human chorionic gonadotrophin (hCG) and follicle stimulating hormone (Griffin, In *Immunological Approaches to Contraception and Promotion of Fertility*, G. P. Talwan, Ed., Plenum Press, New York (1986)). Immunocontraception utilizing antibodies against normally "circulating" antigens poses the problem that immune complexes might form which would bring about undesirable tissue damage. Furthermore, immunization with "circulating" antigens has not proven totally effective in inhibiting fertility.

Immunologically based methods of contraception are preferable to other commercially available methods such as surgical sterilization or birth control pills (for humans and pets) in which there is a continuous expense for medication which must be used and purchased on a regular basis and are only indicated for use on a temporary basis. Thus, a considerable need exists for antigen preparations that can induce transient or permanent contraception in an individual and which can be provided in a safe, reliable and cost effective manner.

SUMMARY OF THE INVENTION

The work of the inventor has focused on the use of purified zona pellucida antigens for immunological sterilization or contraception. Immunization with zona pellucida antigens has distinct advantages over other immunological contraceptive methods. Immunocontraception with zona pellucida antigens can be designed so that it is not abortive but instead inhibits fertilization. This is particularly desirable for immunocontraception in humans. In addition, this method may be modified so that ovarian follicular development is inhibited causing permanent sterilization. This modification will allow non-surgical sterilization of pets and other animals Without the concurrent surgical risks and expense.

Another distinct advantage to zona pellucida protein immunocontraception is the fact that low liters of zona pellucida antibodies will block fertilization. This is due to the localized and specific nature of the site of action of the immunocontraceptive antibody and the limited occurrence of naturally occurring zona pellucida protein in the individual in which fertilization is to be blocked. The zona antigens studied to date are tissue specific and are fixed in the ovary so they do not circulate. In contrast, the hormone proteins circulate throughout the individual, occur at much higher levels, and the levels of circulating antigen vary greatly depending upon the physiological state of the individual. In addition, the levels of sperm antigens which must be blocked for sperm antigen immunocontraception to be efficient is variable, being dependent upon the amount of sperm in the vaginal canal and uterine cavity.

Since the ZP proteins of a variety of animal species are immunologically crossreactive, the necessity for developing an immunizing antigen for each species in which contraception is desired is obviated.

One object of the present invention was the development of an effective immunological method of contraception which (1) requires only one (or minimal) numbers of administrations and therefore does not require the continuous need for a physician (if human use) or veterinarian (if animal use) and (2) can be designed to induce permanent sterilization or castration (desirable in pets) or transient infertility (desirable in humans as well as breeding pets).

One of the disadvantages prior to the present invention was the limited supply of zona pellucida antigens and antibodies to use for immunocontraception. The present invention provides a plentiful readily available source of zona pellucida antigens and antibodies for immunocontraception by providing zona pellucida antigens produced by recombinant DNA technology and monoclonal zona pellucida antibodies and ZP anti-idiotypic antibodies. This provides an additional cost effective advantage since antigens and antibodies are able to be manufactured on a large cost effective scale using recombinant DNA and hybridoma technology.

The present invention relates to antigenic preparations and methods of immunizing an animal to induce antibodies which react with epitopic determinant found on zona pellucida antigens. This invention also relates to monoclonal anti-zona pellucida antibody, to novel hybridoma cells which express such antibody, and to a method for producing such hybrid cells and anti-zona pellucida antibody. In addition, the present invention relates to anti-idiotype zona pellucida monoclonal antibodies and the use thereof for active immunocontraception.

It is established-that an individual antigen (e.g., a glycoprotein) may have multiple antigenic determinants or "epitopes" which can be recognized by antibodies. These epitopes may include amino acid sequences, carbohydrate residues, conformational or "shape" determinants, or the site at which two different molecules or peptides interact. The glycoproteins of zona pellucida structure contain all of these types of determinants (Drell and Dunbar, *Biol. Repro.* 30:445 (1984); and Timmons et al., *Biol. Repro.* 36:1275 (1987).

In a primary embodiment of the invention, an antigen preparation is produced which contains the polypeptide portion of the zona pellucida protein antigens using recombinant DNA techniques. In another embodiment of the invention, an antigen preparation which contains the polypeptide determinant site of zona pellucida protein is produced using recombinant DNA techniques. These recombinant polypeptides, and analogs thereof, are hereinafter referred to collectively as recombinant zona pellucida protein(s).

The term "zona pellucida" protein is intended to include polypeptides having the same amino acid sequence as the naturally occurring and recombinant zona pellucida protein (s) and analogs thereof. The term analogs is intended to include proteins or polypeptides which differ from zona pellucida protein by addition, deletion or substitution of one or more amino acids providing that said polypeptide demonstrates substantially the antigenic and biologic activity of zona pellucida protein. These analogs include selected determinant sites of the zona pellucida protein. These antigenic preparations can be used to immunize an animal such that antibodies are produced thereto.

Pharmaceutical compositions comprising the antigen preparation of the invention and immune response-enhancing components, together with pharmacologically appropriate carriers, are also included in this invention. Thus, in one embodiment the invention comprises a substantially purified polypeptide comprising the amino acid sequence of the zona pellucida protein or parts thereof, expression vehicles comprising a DNA sequence coding for said zona pellucida protein, hosts transformed with said expression vehicle, methods of producing the zona pellucida protein in hosts, and methods of inducing the production of antibodies in an animal to zona pellucida antigens comprising immunizing said animal with a pharmaceutical composition comprising the recombinant zona pellucida protein.

In another embodiment, the present invention comprises monoclonal anti-zona pellucida antibodies, novel hybridoma cells which express such antibodies and to a method of immunocontraception utilizing such monoclonal antibodies.

Fusion between myeloma cells and spleen cells from immunized donors has been shown to be a successful method of deriving homogeneous antibodies. Thus, continuous cell lines of genetically stable hybridoma cells capable of producing large amounts of monoclonal antibodies against malignant tumors and specific viruses and their antigenic determinants have been developed. According to U.S. Pat. No. 4,172,124 to Koprowski et al., antibodies demonstrating a specificity for malignant tumors can be produced by somatic cell hybrids between hypoxanthine phosphoribosyltransferase deficient myeloma cells and spleen or lymph cells derived from an animal previously primed with tumor cells. Also, according to U.S. Pat. No. 4,196,265 to Koprowski et al., continuous cell lines of genetically stable fused cell hybrids capable of producing large amounts of monoclonal antibodies against specific viruses and their antigenic determinants have been developed.

Such cell fusion techniques can also be employed to provide a reliable and standard supply of anti-zona pellucida antibodies, e.g., immunocontraceptive antibodies.

Immunization of an individual may be achieved actively or passively. The term "active immunization" means that an antigen or immunogen is administered to an individual and the individual's immune system produces antibodies against the antigen. The immunizing antigen may be any substances to which a body will produce antibodies. Antigens effective in the present invention to actively immunize an individual to produce contraception or sterilization include recombinantly produced ZP antigen (rZP), whether glycosylated or not, as well as anti-idiotypic ZP antibodies. The term "passive immunization" means that antibodies produced outside of the individual in vitro or in another individual are administered to the individual in order to produce immunocontraception. The ZP monoclonal antibodies of the present invention when administered to an individual produce such passive immunization.

Passive immunization with monoclonal antibodies to ZP antigens causes transient (preferably several months) infertility. The anti-zp monoclonal antibody inhibits fertilization by interfering with sperm binding to or penetration of the zona pellucida without having adverse effects on ovarian function. Thus, the method of immunocontraception of the present invention may be effected passively by administration of monoclonal antibodies directed agent zona pellucida antigens or actively by administration of zona pellucida antigens produced by recombinant DNA technology or anti-idiotype monoclonal antibodies.

When a homogeneous antibody (e.g., a monoclonal antibody) is used as an antigen, portions of the molecule may be recognized as antigenic determinants by the responding is immunized host. The unique combination sites of the homogeneous antibody which would recognize its antigenic determinants is termed the "idiotype." Antibodies produced against these sites of the antibody are therefore termed "anti-idiotype." These antibodies may have "internal images" and therefore can have activities which mimic the original immunogen (Sege, K. and Peterson, P. A., *Proc. Soc. Natl. Acad. Sci. (USA)* 75:2443 (1978); Schreiber et al., *Proc. Soc. Natl. Acad. Sci. (USA)* 77:7385 (1980)).

A monoclonal antibody (PSI) which recognizes a carbohydrate moiety of ZP which will inhibit sperm from binding to the surface of the zona pellucida as shown in FIG. 8. The PSI monoclonal antibody may be used as an immunogen (antigen) for the production of anti-idiotype antibodies which can then be used for immunological sterilization or contraception.

The anti-zona pellucida monoclonal antibody binding determinant genes may be cloned and modified by recombinant DNA technology to produce "single chain antibodies" directed against ZP antigenic determinants (Cabilly et al., *Proc. Acad. Sci. USA* 81:3273 (1984); Boss et al., *Nucleic Acids Research* 12:3791 (1984)).

BRIEF DESCRIPTION OF THE FIGURES

FIG. 2 shows the N-terminal amino acid sequence of 3 PIG ZP proteins I(E) [SEQ ID NO: 7; I(T) [SEQ ID NO: 8]; II(E) [SEQ ID NO: 9]; and III(E) [SEQ ID NO: 10] and 2 rabbit ZP proteins (I(E) [SEQ ID NO: 5]; and II(E) [SEQ ID NO: 6]

FIGS. 4A–4B show the DNA sequence of 3 clones which express ZP antigen.

FIGS. 7A–F show results of active immunization on ovarian function in rabbits.

BRIEF DESCRIPTION OF THE PREFERRED EMBODIMENTS

Figure 1:
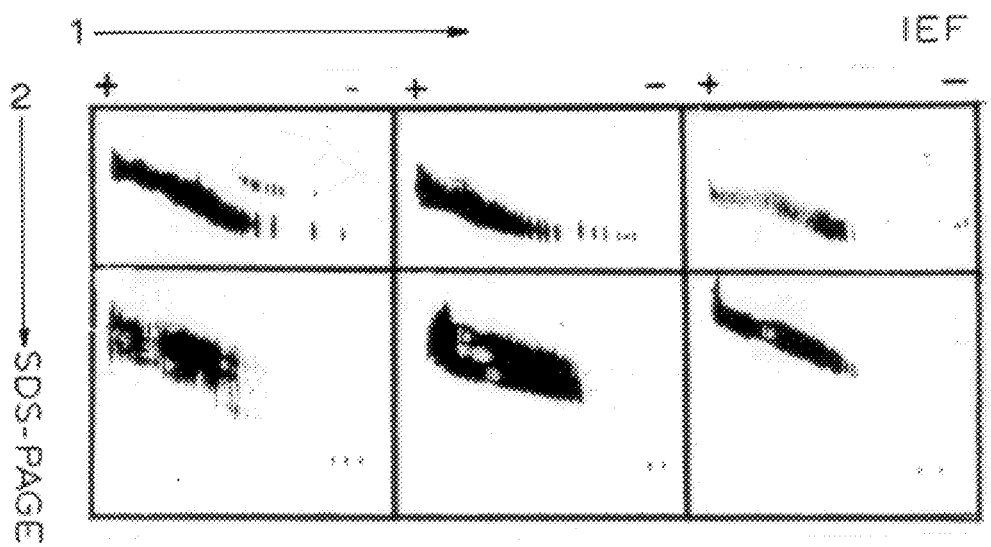
FIG. 1 demonstrates the identification of antibodies recognizing ZP antigens used to screen the library by 2D-PAGE gel immunoblot method.

At its most fundamental levels, the invention comprises genetically engineered antigen preparations of the zona pellucida and methods of utilizing these antigen preparations to stimulate the immune system of an animal and induce the production of antibodies to zona pellucida antigens in order to prevent fertilization, implantation or the development of the follicles and subsequent hormone producing function of the ovaries.

The inventor has devised a method of producing cDNA molecules which code for the zona pellucida antigen using recombinant DNA techniques. ZP cDNA is inserted into the expression vectors λgt11. This expression vector is used to transform *E. coli*. Clones expressing ZP protein or determinants thereof are identified by ZP antibody binding. DNA isolated from the single stranded phage is then used for the expression of the ZP antigen and as a template for the production of DNA copies and cDNA. The insert of the λgt11 phage DNA encoding the ZP DNA sequence is then inserted into the pEx vector which is used to transform a bacterial host in which the DNA is expressed, producing quantities of the ZP antigen which can be used for immunocontraception.

The M13 cloning procedure (Sanger et al., *Proc. Acad. Sci. USA* 74:5463 (1977)) has been used to determine the partial DNA sequence of three of the 9 cDNA expression clones which have been selected by screening λgt11 expression libraries with affinity purified ZP antibodies. Briefly, this cloning procedure comprises the dideoxy chain termination method in which the zona pellucida DNA is cloned into the filamentous bacteriophage M13.

When the zona pellucida genes are expressed in the prokaryotic host *E. coli*, the polypeptide which is produced is not glycosylated; hence, the molecular weights of the major pig ZP polypeptides are approximately 35, 55 and 80 Kd; and the molecular weights of the major rabbit ZP polypeptides are 50, 75, 85 Kd (Table 1) which are lower than that observed for the glycosylated molecules (Table 1). The zona pellucida protein produced in, for instance, prokaryotes from the zona pellucida DNA coding for the zone pellucida polypeptide is termed "rZP" or "recombinant zona pellucida protein." In addition, when a gene coding for the zona pellucida protein is produced in eukaryotes, the protein may be glycosylated and the glycosylated protein is termed "rgZP." The term "immunologically related antigens" is meant to denote those antigens with significant genomic homology to zona pellucida protein such that the products expressed by these DNA show significant levels of immunologic cross-reactivity An example of such an immunologically related antigen is a polypeptide containing more or less amino acids than the naturally occurring ZP antigen which has significant immunological or biological cross reactivity with the zona pellucida polypeptide.

The term "host" as used in the present invention is meant to include not only prokaryotes but also eukaryotes such as yeasts and filamentous fungi as well as plant and animal cells.

The term "prokaryote" is meant to include all bacteria which can be transformed with the DNA for the expression of the zona pellucida or rZP protein.

The term "eukaryote" is meant to include all yeasts, fungi, animal and plant cells which can be transformed with the DNA for the expression of the zona pellucida, or rZP protein.

The DNA for the zona pellucida protein can be derived from any mammalian species. All that is required is that the genetic sequence for the glycoprotein be expressed in the prokaryotic or eukaryotic organism. Preferred is the zona pellucida DNA which expresses ZP protein(s) from pig or rabbit. Especially preferred is the sequence of the zona pellucida DNA which is immunologically cross reactive among multiple animal species (e.q., pig, rabbit, dog, cat or human).

A recombinant DNA molecule coding for the zona pellucida protein can be used to transform a host using any of the techniques commonly known to those of ordinary skill in the art. Especially preferred is the use of a vector containing the zona pellucida coding sequence for purposes of prokaryote transformation.

The zona pellucida recombinant protein (rZP) of the invention could have more or less amino acids at its flanking ends as compared to the amino acid sequence of native zona pellucida proteins.

The term "substantially pure" when applied to the zona pellucida protein of the present invention means that the polypeptide is essentially free of other ovarian proteins normally associated with the zona pellucida protein in its natural state and exhibiting constant and reproducible electrophoretic or chromatographic response, elution profiles, and antigen activity. The term "substantially pure" is not meant to exclude artificial or synthetic mixtures of the zona pellucida protein with other compounds.

Methods for preparing fused, operably linked genes and expressing them in bacteria are known and are shown, for example, in U.S. Pat. No. 4,366,246, herein incorporated by reference. The genetic constructs and methods described therein can be utilized for expression of zona pellucida protein in prokaryotic or eukaryotic hosts.

Prokaryotic hosts may include Gram negative as well as Gram positive bacteria, such as *E. coli, S. tymphimurium, Serratia marcescens*, and *Bacillus subtilis*.

Eukaryotic hosts may include yeasts such as *Pichia pastoris* or mammalian cells.

In general, expression vectors containing promoter sequences which facilitate the efficient transcription of the inserted DNA fragment are used in connection with the hose. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Examples of promoters which can be used in the invention include, but are not limited to: rec A, trp, lac, tac, and bacteriophage lambda pR or pL. Examples of some of the plasmids or bacteriophage which can be used in the invention are listed in Maniatis et al., *Molecular Cloning*, Cold Spring Harbor Laboratories, 1982, and others are known to those of skill in the art and can be easily ascertained.

The invention extends to any host modified according to the methods described, or modified by any other methods, commonly known to those of ordinary skill in the art, such as, for example, by transfer of genetic material using a lysogenic phage, and which yield a prokaryote or eukaryote expressing the gene for zona pellucida protein.

A gene is a DNA sequence which encodes through its template or messenger RNA a sequence of amino acids characteristic of a specific peptide. The term cDNA includes genes from which the intervening sequences have been removed. By the term rDNA is meant a molecule that has been recombined by splicing cDNA or genomic DNA sequences in vitro.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance or ampicillin resistance. The word "vectors" is sometimes used for cloning vehicle.

An expression vehicle is a vehicle similar to a cloning vehicle but which is capable of expressing a given structural gene in a host, normally under control of certain control sequences.

Hosts transformed with the zona pellucida genome for zona pellucida proteins are particularly useful for the production of zona pellucida polypeptide and protein which can be used for the immunization of an animal. As stated previously, when the genome for zona pellucida protein is expressed in bacteria, glycosylation does not occur. Hence the full length recombinant zona pellucida proteins has molecular weights which are lower than the native molecules (see Table 1).

The recombinant zona pellucida protein may comprise the entire amino acid sequence of the zona pellucida protein or may comprise only a specific determinant. An animal immunized with zona pellucida recombinant protein will produce antibodies which will bind to epitopes present an the recombinant or naturally occurring polypeptides. Thus, the commercial production of zona pellucida-containing recombinant proteins can be carried out.

The term "immunogenically effective amount," as used in the invention, is meant to denote that amount of zona pellucida antigen which is necessary to induce the production in an animal of antibodies which will bind to zona pellucida epitopes.

The term "individual" is meant to include any animal, preferably a mammal, and most preferably a cat, dog, cow or human.

The zona pellucida recombinant proteins of the invention is particularly useful in sensitizing the immune system of an animal such that, as one result thereof, antibodies reactive with epitopes present on the zona pellucida are produced.

Immunization of an individual may be achieved actively or passively. The term "active immunization" means that an antigen or immunogen is administered to an individual and the individual's immune system produces antibodies against the antigen. The immunizing antigen may be any substance to which a body will produce antibodies. Antigens effective in the present invention to actively immunize an individual to produce contraception or sterilization include recombinantly produced ZP antigen (rZP), whether glycosylated or not, as well as anti-idiotypic ZP antibodies. The term "passive immunization" means that antibodies produced outside of the individual in vitro or in another individual are administered to the individual in order to produce immunocontraception. The ZP monoclonal antibodies or genetically engineered single chain antibodies of the present invention when administered to an individual produce such passive immunization.

When an individual is immunized with ZP antigens or anti-idiotypic antibodies prior to the maturation of the ovaries, ovarian development is severely hindered and permanent irreversible sterilization may occur. This is a particularly desirable method of causing immunocontraception in animals, particularly pets such as cats and dogs, when reproduction is undesirable. The use of ZP immunocontraception in such cases obviates the need for costly and potentially dangerous surgical contraception.

Preferred for immunocontraception are zona pellucida peptides which are immunologically cross reactive among species. Especially preferred are DNA's encoding the zona pellucida derived from pig or rabbit ovaries.

In another embodiment this invention contemplates a novel continuous hybridoma cell line which expresses monoclonal anti-zona pellucida antibody, to the use of such cell line in production of such antibody, and to a method for producing such cell line. The invention also contemplates a method for obtaining large amounts of anti-zona pellucida antibody for use in passive contraception.

According to the present invention a novel continuous hybridoma cell line which expresses anti-zona pellucida antibody is obtained by immunizing an animal with zona pellucida protein, preferably recombinant zona pellucida protein and most preferably to nature zona pellucida antigens, forming fused hybrid cells between antibody-producing cells from the immunized animal and myeloma cells, cloning the hybrids and selecting clones which express anti-zona pellucida antibody. More specifically, a mouse or other animal is injected with purified zona pellucida antigen and the antibody producing cells of the animal's spleen are then fused with a cancerous type of mouse cell or myeloma cell. The hybrid cell so formed produces the anti-zona pellucida antibody molecule of its spleen cell parent and continually grows and divides like its parent myeloma cell. The clone of cells producing such antibody are selected and grown as a continuous cell line from which large amounts of anti-zona pellucida antibody is harvested.

In the alternative, the clonal hybrid cells may be injected into a histocompatable animal where they proliferate, producing high levels of anti-zona pellucida antibody which can be recovered from the animal's ascites fluid.

Thus, the present invention makes available on a relatively large scale a reliable and standard supply of anti-zona pellucida antibody for use in immunocontraception.

The term "immunocontraception" is meant to include temporary, reversible contraception, and permanent non-reversible contraception or sterilization resulting from immunological methods of intervention.

This invention includes the use of monoclonal ZP antibodies for passive immunization resulting in transient infertility or the use of anti-idiotypic antibodies which mimic the structure of the native antigen (Erlanger et al., *Immunological Rev.* 94: 25, 1986) for active immunization.

The zona pellucida recombinant proteins and monoclonal antibodies can be administered parenterally by injection, long release implants, rapid infusion, intravenously, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable liquid dosage forms include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing the zona pellucida recombinant proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example. AlK(SO4)2, Alna (SO4)2, AlNH4(SO4), silica, alum, Al(OH)3, Ca3(PO4)2, kaolin, and carbon), polynucleotides (for example, poly IC and poly AU acids), and certain natural substances (for example, wax D from *Mycobacterium tuberculosis*, as well as substances found in *Corynebacterium parvum, Bordetella pertussis*, and members of the genus *Brucella*).

The zona pellucida antigen preparations of the invention can be used in an animal to induce the production of antibodies which will bind to epitopic determinants of zona pellucida. A particularly useful method in enhancing the production of antibodies to zona pellucida is to first immunize an animal with the zona pellucida antigenic preparation of the invention followed by a later second immunization.

The age of the animal at the time of initial immunization may be critical. For permanent immunocontraception or sterilization, it is most preferable that the animal be immunized 2–3 months before the onset of puberty since at this age the most pronounced interference with ovarian maturation occurs. For reversible contraception, a ZP antigen expressed late in ovarian follicular development can be used.

One way of determining whether an animal has been immunized is by determining the animal's immune status with respect to zona pellucida antigens. This evaluation can be done by using the zona pellucida recombinant proteins of the invention in an immunoassay such as, for example, an ELISA assay (Drell and Dunbar, *Biol. Reprod.* 30:445, 1984) to detect antibodies to zona pellucida. In so doing, it is possible to determine when the individual's antibody titer to zona pellucida is sufficiently high to ensure immunization and protect against pregnancy.

Many different techniques exist for the timing of the immunizations when a multiple immunization regimen is utilized. It is possible to use the antigenic preparation of the invention more than once to increase the levels and diversity of expression of the immunoglobulin repertoire expressed by the immunized animal. Typically, if multiple immunizations are given, they will be spaced 1 month to 6 months apart.

Generally, the dosage of zona pellucida recombinant protein administered to an animal will vary depending on such factors as age, condition, and whether contraception or ovarian castration is the object of the immunization, and other variables which can be readily ascertained and adjusted by one of ordinary skill in the art.

The antigenic preparations of the invention can be administered as either single or multiple dosages and can vary from 0.01–5 g/ml for the zona pellucida antigen per dose, more preferably 0.05–1.0 g/ml zona pellucida antigen per dose, most preferably 0.1–0.5 g/ml zona pellucida antigen per dose.

Having now generally described the invention, a more complete understanding can be obtained by reference to the following specific examples. These examples are provided for purposes of illustration only and are not intended to be limiting unless otherwise specified.

EXAMPLE 1

ISOLATION OF ZP PROTEIN AND PREPARATION OF POLYCLONAL ANTIBODIES

A. Isolation of Zona Pellucida (ZP)

Zona pellucidae (ZP) were isolated using the methods described by Wood et al., *Biol. Repr.* 25(2):439 (1981).

An instrument consisting of two wheels (10 cm in diameter) containing 50 rows of ganged razor blades separated by stainless steel washers (2 mm) was utilized to rupture ovarian follicles. One of the two wheels was held stationary, while the second was attached to a rotating handle connected to one of the wheels by a chain. Ovaries were dropped between the razor blade wheels submerged in a plexiglass tank containing 6 liters of 0.01M phosphate buffered saline (PBS), pH 7.2, with 2 mM sodium citrate and 2 mM EGTA. After passing about 300 ovaries through the razor blade wheels, the ruptured ovaries settled on the bottom of the plexiglass tank on a removable 1000 μm mesh nylon screen. The ovaries were then separated from the buffer by removing the screen, and were washed thoroughly to remove any oocytes which adhered to the ovaries. The oocytes and zona pellucida were then isolated by sieving through various sizes of nylon mesh screens. The oocytes were homogenized and washed through a 50 micron mesh nylon screen so that the zona were retained. Approximately 100,000 to 300,000 ZP can be isolated in an 8 hour period using this procedure.

B. Purification of ZP Proteins

ZP proteins were purified using high resolution two dimensional polyacrylamide gel electrophoresis (PAGE) as previously described by Dunbar et al., *Biol. Repr.* 24:1111 (1981), incorporated herein by reference. This method separates proteins by isoelectric focusing (IEF) in the first dimension and sodium dodecyl sulfate (SDS) polyacrylamide gel electrophoresis (PAGE) in the second dimension.

A pellet of about 30,000 zonae (1 mg protein) was resuspended in 300 μl solubilization buffer 2% SDS, 2% β-mercaptoethanol, and 1% cyclohexylaminoeth sulfonic acid (CHES) in water pH about 9.5–9.6). Forty microliters were applied to each 4% PAGE (with 1.8% bisacrylamide crosslinker) gel. Ampholines (LKB) with a wide pH range of 3.5–10 were incorporated into the PAGE gel, and gels were focused for 16 h at 400 V at 25° C. after prefocusing for 2 h at 200 V.

Slab gels (10–20% gradients of polyacrylamide with 0.8% bisacrylamide crosslinker) were used for the second dimension SDS PAGE. The gels were electrophoresed at about 3 amps until the dye front had reached the bottom of the gel, i.e., at room temperature. Proteins are identified by either Coomassie blue staining or silver staining. ZP antigens have unique protein profiles which exhibit heterogeneity in both charge and molecular weight (Table 1) due to their extensive glycosylation. ZP antigens were identified by immunoblot as shown in FIG. 1 after electrophoretic transfer to nitrocellulose as described below. The ZP proteins were eluted from the gels electrophoretically. ZP protein N-terminal sequence determination was carried out by the method of Hunkapillar et al., *Meth. Enzymol.* 91:227 (1983).

The molecular weights of the major pig ZP polypeptides are approximately 35, 55 and 80 Kd; and the molecular weights of the major rabbit ZP polypeptides are 50, 75, 85 Kd (Table 1) which are lower than that observed for the glycosylated molecules (Table 1).

TABLE 1

Table of Estimated Molecular Weights of Glycosylated and Deglycosylate Pig and Rabbit ZP Proteins

|  | Mol. Weight range | Enzyme Deglycosylated | TFMS Deglycosylated |
|---|---|---|---|
| deglycosylate |  |  |  |
| PIG ZP I | 40–110K | 42K | 35K |
| ZP II | 70–110K | 60K | 55K |
| ZP III | 95–118K | 80K | 80K |
| Rabbit |  |  |  |
| I | 68–125K | 65K | 50K |
| II | 81–100K | 80K | 75K |
| III | 100–132K | 90K | 85K |

EXAMPLE 2

Preparation of Polyclonal ZP Antibodies

Polyclonal antibodies were prepared by immunizing female rabbits or castrated male sheep with 300 to 500 μg of total heat solubilized zona pellucida (HSZP) (60°–65° C. in 0.01M sodium carbonate buffer, pH 9.5 for 1 to 2 hours). Alternatively, approximately 50 to 200 μg of purified ZP proteins isolated by 2D-PAGE gels were used for immunization. All protein samples were suspended in 1 ml water and were emulsified with Complete Freund's adjuvant prior to injection. Animals were injected in multiple intradermal sites and subscapularly and were boosted after 4 weeks with ZP proteins at one half the amount of protein used for the initial immunization in Incomplete Freund's adjuvant. In some instances, additional boosts at monthly intervals using Complete Freund's adjuvant were given to obtain higher antibody titers.

Antibodies were analyzed and characterized using the enzyme-linked immunoassay (ELISA) procedure or immunoblotting procedure. The ELISA assay used is the Vecta Stain Kits for detecting rabbit, sheep or mouse immunoglobulin available from Vector Laboratories. For this assay 50–100 μg of HSZP protein in 0.1M NaCO$_3$, pH 9.0 was added to wells of 96-well microtiter trays. The assay was then carried out according to methods known to those of ordinary skill and provided in the kit instructions. For immunoblotting, the previously described method of Timmons et al., *Biol. Repr.* 36:1275 (1987), incorporated herein by reference, was used to identify specific ZP glycoproteins and peptides. Unstained, unfixed 2D-PAGE gels were placed on the cathode side of the nitrocellulose paper (Bio-Rad) and transferred for 2.5 h at 1.3 A using the E-C electroblot transfer unit. The nitrocellulose paper was then blocked overnight in 10 mM Tris(hydroxymethyl)aminomethane (Tris)-saline, pH 7.2, with 3% (w/v) bovine serum albumin (BSA) and 0.01% sodium azide (Tris-saline-azide (BSA)), followed by washing with two changes of Tris-saline-azide (without BSA). Polyclonal serum (1–5 ml), or monoclonal antibody supernatant (containing 100 μg/ml immunoglobulin G (IgG), was diluted in 50 ml Tris-saline-azide (BSA) and incubated with the nitrocellulose transfer at 25° C. with shaking overnight, followed by washing with two changes of Tris-saline-azide (without BSA).

The nitrocellulose transfer was then incubated with $^{125}$I-protein A for polyclonal serum, or $^{125}$I-goat anti-mouse IgG for monoclonal supernatant. A total of $10^6$ cpm in 50 ml Tris-saline-azide (containing BSA) was added to each transfer and incubated overnight with shaking. Extensive washing in Tris-saline-azide (without BSA) was carried out before air drying and exposure to Kodak XAR-5 x-ray film for autoradiography.

Antibodies were affinity purified using CNBr activated Sepharose conjugated to ZP proteins. CNBr-activated Sepharose 4B resin (Pharmacia) was used to prepare affinity columns. The resin was coupled to either heat-solubilized HSPZ or HSRZ (heat solubilized rabbit zona pellucida protein). ZP preparations of approximately 1 mg/ml were prepared in solubilization buffer, pH 9.6, as described above. The ZP was suspended in coupling buffer (0.1M NaHCO$_3$; 0.5M NaCl, pH 8.3). The resin was washed and allowed to swell in 1 mM HCl and quickly rinsed with the coupling buffer before application of the ZP in coupling buffer which contained 0.5 NaCl to minimize protein-protein interaction. The mixture was rotated slowly at room temperature for two hours. The coupling buffer with unreacted ZP solution was removed and the resin was incubated in 1M ethanolamine overnight at 4° C. with slow rotation to block remaining active groups. The resin was then washed three times each with 1 mM NaHCO$_3$ (pH 8.3, 0.5M NaCl), followed by 0.1M acetate buffer (pH 4, 0.5M NaCl).

Antiserum was incubated with the coupled resin at 4° C. under slow rotation overnight. Before elution, the resin was warmed to room temperature and was washed thoroughly with borate/saline buffer (100 mM boric acid, 75 mM sodium borate, 75 mM NaCl, pH 8.4) to ensure that unbound protein was removed. Elution of the bound IgG was carried out using 200 mM glycine (pH 2.7, 0.8% NaCl). The acid fractions were collected directly into 0.2M Trizma base such that the final solution was Trizma:glycine (1:2) (pH 7.5). This was done to neutralize and thus minimize damage to the eluted purified antibody. Antibody-containing fractions were aliquoted and frozen for analysis. Purification of immunoaffinity antibodies was demonstrated by one-dimensional SDS-PAGE analysis.

EXAMPLE 3

ISOLATION OF cDNA CLONES EXPRESSING ZP PROTEINS

One of skill in the art will recognize that the method of Chirgwin et al., *Biochem.* 18:5294 (1979) can be used to prepare RNA from 6 week, 12 week and greater than 6 month old rabbit ovaries. Preferably, ovaries were frozen in liquid nitrogen and pulverized into a fine powder before homogenization since the ovary contains significant quantities of connective tissues. From 4 to 8 ovaries were homogenized in 4M guanidinium thiocyanate (containing 0.025M sodium citrate, 0.5% sodium laurylsarcosine (w/v), pH 7.0) in the presence of mercaptoethanol. The homogenate was centrifuged at 10,000 rpm in a JA-20 rotor for 10 min at 10° C. The total RNA was isolated from protein by ethanol precipitation or by sedimentation through cesium chloride. Optimal yields of RNA were obtained using cesium chloride sedimentation. The supernatant was layered over 5.7M CsCl containing 3.8 g/100 mls EDTA (disodium salt) and centrifuged in a SW-40 rotor at 32,000 rpm for 20 hours at 20° C. The pellet is resuspended in Guanidine hydrochloride and the RNA precipitated with 0.3 ml of 3M sodium acetate (pH 5.2) and 2.2 volumes of 95% ethanol. After incubation overnight at −20° C., the RNA is recovered by centrifugation at 11500 rpm for 10 min at −5° C. The RNA is washed 2 times with 95% ethanol, and dissolved in water. Recovery of RNA is monitored by measuring the 260/280 absorbance ratio. Polyadenylated RNA was isolated by oligo (dT)-cellulose chromatography as previously described by Maniatis, et al., *Molecular Cloning*, p. 197 et seq., Cold Spring Harbor Laboratory (1982), incorporated herein by reference. The chromatography column fractions were monitored at A$_{260}$ with an ISCO spectrophotometer.

Figure 3:
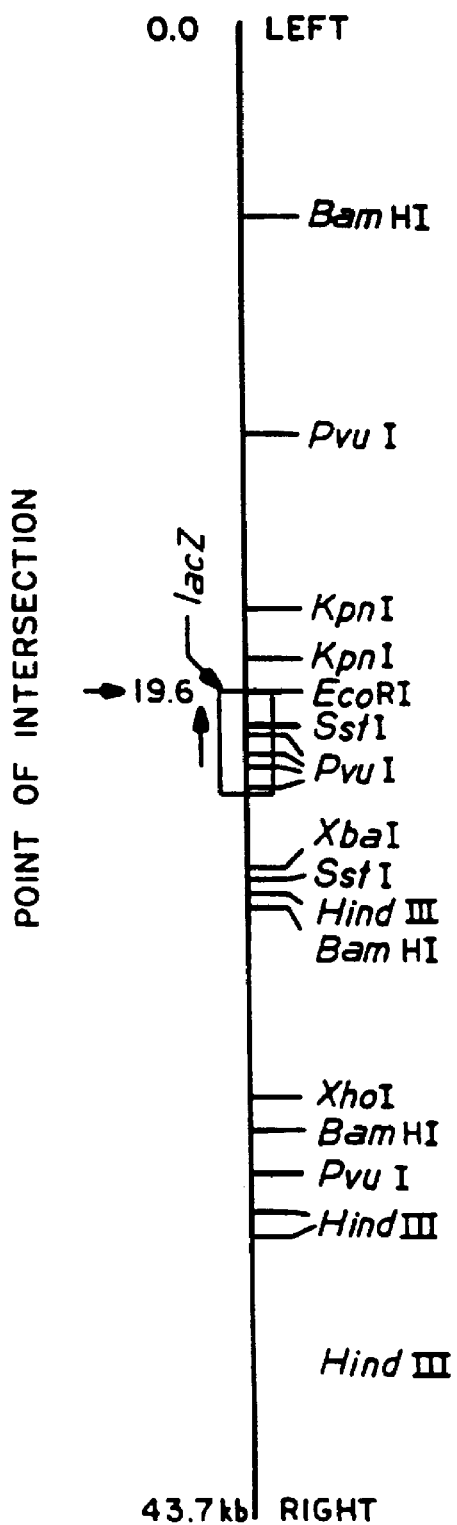
FIG. 3 restriction endonuclease cleavage map of the λgt11 vector which is used to develop the expression library to clone the cDNA for ZP.

Cell-type specific cDNA probes were prepared as described by Davis, et al., *Proc. Natl. Acad. Sci. USA* 81:2194 (1984); and Young et al., *Proc. Natl. Acad. Sci. USA* 80:1194 (1983). The λgt11 vector used for preparation of the expression library is shown in FIG. 3. For cDNA library construction, 2 micrograms of polyA-mRNA isolated from ovarian tissue was used for each cDNA synthesis. First strand cDNA was synthesized with oligo dT priming and addition of reverse transcriptase. After addition of the reverse transcription and incubation for 60 min at 43° C., the reaction is terminated by addition of EDTA. The sample is extracted with phenol:chloroform:isoamyl alcohol (25:24:1). The aqueous phase is removed, the organic phase reextracted with 0.1M NaCl containing 10 mM Tris-HCl containing 1 mM EDTA (pH 8.0). After pooling the aqueous phases, the DNA is precipitated with 2M ammonium acetate followed by addition of 95% ethanol. After freezing and thawing, the solution is centrifuged, redissolved in 25 μl of 10 mM Tris-HCl, 1 mM EDTA (TE). Ten microliters of 7.5M ammonium acetate and 50 μl of 95% of ethanol is added. The RNA-DNA hybrid was then nicked by *E. coli* RNAase H. Second strand cDNA synthesis was carried out by *E. coli* DNA polymerase. The double-strand cDNA was then blunt-ended by T4 DNA polymerase. The cDNA was methylated at the EcoRI sites before ligation to EcoRI linkers. The linkered cDNA was then treated with EcoRI enzyme and purified by chromatography on BioGel P50 (BioRad) and ligated to λgt11 arms obtained from Strategene according to procedures described therewith, Using this procedure approximately 5×10 plaques were obtained for the 6 week and 8 month old rabbit libraries and 1×10$^7$ plaques were obtained for the 12 week rabbit library.

For library screening, 5×10$^3$ plaques were plated per 100 mm plate. Plaques were then transferred to IPTG saturated nitrocellulose paper and probed with affinity purified antisera prepared as described in Example 2.

In order to isolate cDNA's expressing protein sequences which are similar in multiple species, polyclonal antibodies against rabbit ZP protein were affinity purified on porcine ZP columns (ZP protein conjugated to cyanogen bromide activated sepharose prepared as in Example 2). Antibodies which eluted with 0.1M glycine (pH 2) are those that recognize antigens associated with both rabbit and pig ZP proteins.

Clones (S1 [SEQ ID NOS: 1 and 2 respectively], P2 [SEQ ID NO: 3], and P3 [SEQ ID NO: 4]) λgt11-S1, λgt11-P1, λgt11-P2 and λgt11-P3 which expressed ZP antigens were subcloned. These subclones were cloned into the M13 phage to sequence the cDNA using the Sanger dideoxy nucleotide chain termination method. (Sanger, et al. *Proc. Natl. Acad. Sci. USA* 74:5463, 1977). The sequence obtained using this method for three of the cDNA clones expressing ZP antigens is shown in FIGS. 4A–4B.

Figure 5:
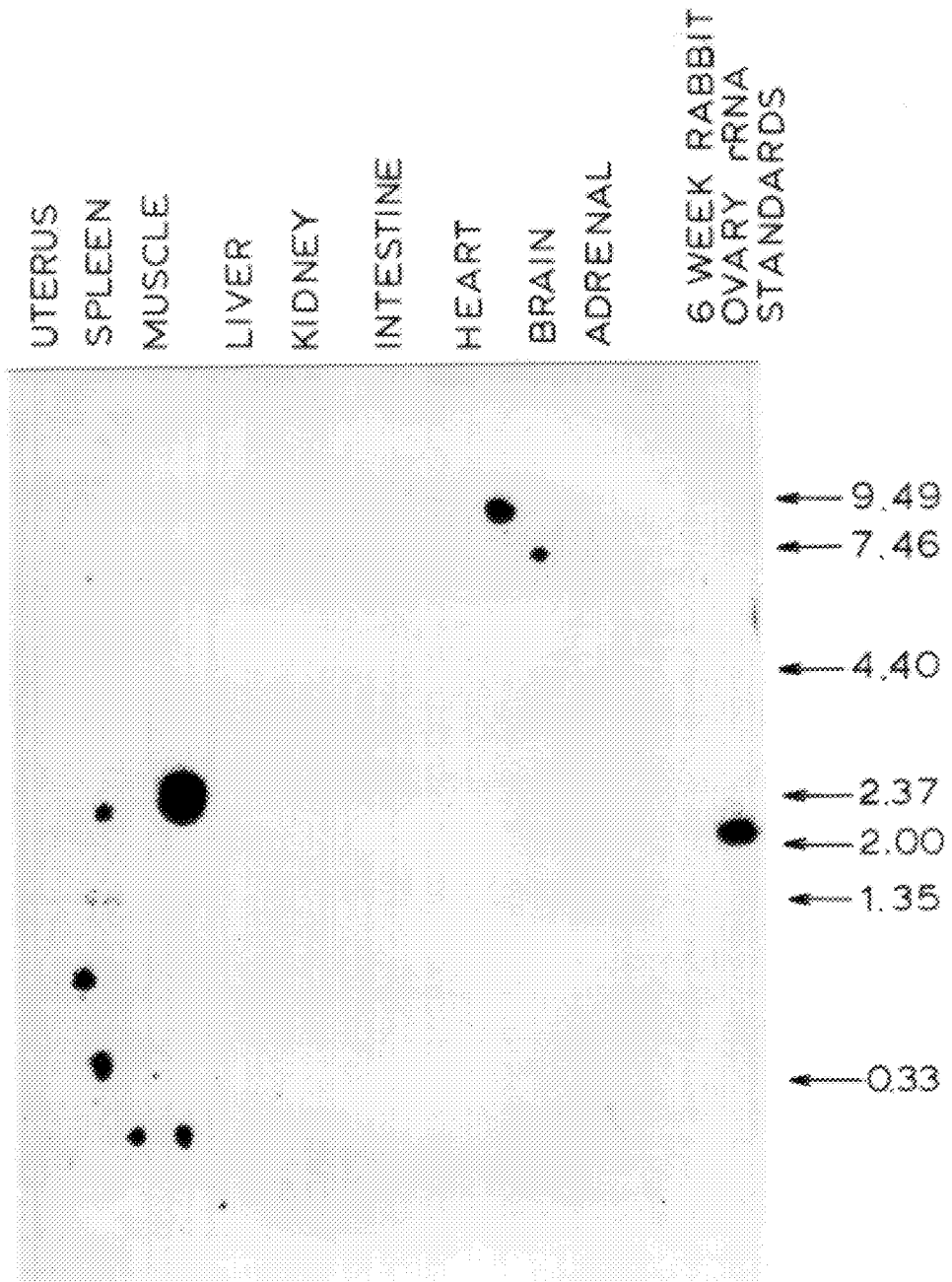
FIG. 5 shows a northern blot analysis demonstrating presence of ZP RNA in ovary but not other tissues.

Northern blot analysis was used to demonstrate that the RNA for ZP protein recognized by two of the cDNA clones (P2 and P3) is present in the ovary but not other tissues. FIG. 5 demonstrates one of these analyses which was carried out using "northern blot" and "dot blots" hybridization of labeled probe to RNA samples. Briefly, for the Northern blot analysis, the total RNA was isolated from ovaries as well as other tissues including liver, kidney, brain, and muscle. The RNAs were denatured and electrophoresed on a formaldehyde agarose gel and then transferred from agarose gel to the solid support of biodyne membrane. The membrane is placed between two filter papers for the transfer and is then air dried and baked for 2 hours at 80° C. The specific ZP cDNAs which were inserted into the λgt11 bacteriophage were digested by EcoRI, and then the insert resolved from the cloning vector by 1% low melting temperature agarose electrophoresis. Under UV light, the insert DNA molecules were identified with ethidium bromide and were excised from the gel for radioactive labeling. cDNA was labeled according to the random oligo-priming method of Feinberg and Vogelstein, *Anal. Biochem.* 132:6 (1983). The labeling reaction is carried out by addition of denatured cDNA to reagents containing $^{32}$P-dCTP, Klenow fragment, BSA, mixed primer, and oligo labeling buffer. The labeled DNAs were separated from unincorporated dCTP by chromatography on a column of Sephadex G-50. For DNA-RNA hybridization, the RNA transferred biodyne membranes are placed into heat-sealable polyethylene bags separately. The prehybridization solution is added into the bag and the bag immersed in a 42° C. water bath overnight. The prehybridization solution was removed and replaced with hybridization solution containing $^{32}$P-labeled DNA probe and immerse in 42° C. water bath overnight. Finally, the membrane was washed several times and exposed to X-ray films with lightning plus screens. The film was exposed for 48 hours at 70° C. prior to development.

Example 4

Expression of ZP Proteins by Recombinant DNA

Recombinant ZP proteins (rZP) are expressed in these prokaryotic or eukaryotic expression systems.

Recombinant λgt11 phage, λgt11-S1 λgt11-P1, λgt11-P2 and λgt11-P3 prepared as described in Example 3 are used to infect *E. coli* Y1089 by incubating the phage with *E coli* Y1089 for 20 min at 32° C. in Luria Broth (LB) medium containing 10 mM MgCl$_2$. Colonies are grown at 32° C. and single colonies tested for temperature sensitivity by transfer to 42° C. Colonies that grow at 32° C. but not at 42° C. are considered to be lysogenic, and comprise approximately 10–70% of the population. Single colonies of the recombinant lysogen are isolated, used to inoculate LB medium, and grown at 32° C. The culture is transferred to 42° C. when the O.D. 600 is about 0.5 and incubated a further 20 min. Transcription of the cloned gene is stimulated by the addition of isopropyl β-D thiogalactopyranoside (IPTG) to a final concentration of 10 mM and the culture incubated at 37° C. for 60 min. The transformed *E. coli* are harvested by centrifugation, resuspended in 50 mM Tris (pH 7.5) and frozen. Lysis occurs upon thawing of the cells, releasing the fusion ZP protein.

The bacteriophages containing ZP DNA designated λgt11-P1 and λgt11-P3 were deposited with the American Type Culture Collection (ATCC), Rockville, Md., U.S.A., Deposit Accession Nos. 40377 and 40378, respectively, on Oct. 8, 1987. The bacteriophage containing ZP DNA designated λgt-11 P2 was deposited with the A.T.C.C Accession No. 40642 on Aug. 4, 1989. The deposits are available pursuant to the patent laws and regulations of the United States and of those countries foreign to the United States in which counterparts of this application are filed. The availability of a deposit does not constitute a license to practice the invention of this application in derogation of any patent issued thereon or on any division or continuation of this application.

In another embodiment the pEX plasmids described by Stanley and Luzio, *EMBO* 3(6):1429 (1984) is used to transform *E. coli* Y1090. The pEX vector expresses a hybrid protein which is insoluble. Isolation of bacteriophage λ DNA will be carried out on the recombinant λgt11 phage following the procedure described by Maniatis et al., *Molecular Cloning: a Laboratory Manual*, Cold Spring Harbor Laboratory (1982), incorporated herein by reference. *E. coli* Y1090 grown in LB medium supplemented with 10 mM MgCl$_2$, 0.2% maltose and 50 µg/ml Ampicillin (Amp) are infected with recombinant λgt11 phage and incubated at 37° C. for 20 min. Infected *E. coli* are plated on LB plates in LB media with 0.7% agarose, MgCl$_2$ and Amp, and incubated overnight at 43° C. Phage are be collected in SM media (0.02M Tris-HCl, pH 7.5; 0.01M NaCl; 0.001M MgSO$_4$. 7H$_2$O) (pH 7.5) and 0.01% gelatin in 1 liter water) and bacteria removed by centrifugation at 8,000×g for 10 min at 40° C. RNase A and DNase I are added to the supernatant containing the phage at final concentrations of 1 µg/ml and incubated for 30 min at 37° C. An equal volume of SM containing 20% polyethylene glycol and 2M NaCl is then added and the suspension incubated at 0° C. for 1 hr, followed by centrifugation at 10,000×g for 20 min at 4° C. The supernatant is removed, and pellet containing the phage resuspended in 0.5 ml M medium. To remove remaining debris, the solution is centrifuged at 8,000×g for 2 min at 4° C., and 5 µl of 10% SDS and 5 µl 0.5M EDTA (pH 8) is added to the supernatant and incubated at 68° C. for 15 min. Sequential extractions with phenol, phenol:chloroform:isoamyl alcohol (25:24:1), and chloroform:isoamyl alcohol (24:1) are performed, harvesting the aqueous phase in each step. An equal volume of isopropanol is added to the aqueous phase and the solution stored at −70° C. for 20 min. After centrifugation for 10 min at 4° C. the pellet is washed with 70% EtOH, dried, and resuspended in 50 µl TE. EcoRI restriction enzyme digestion is carried out following standard procedures on an aliquot of the isolated DNA. After digestion is complete, Tris boronate EDTA loading buffer (TBE) 90 mM Tris borate, 90 mM boric acid, 2 mM EDTA) is added at 1:1 ratio and loaded on 1.4% agarose gel. The gel is run at 100 V until the xylene cyanole front is midway through the gel, the DNA bands are visualized by ultraviolet light and bands of the predicted size removed. Electroelution will be carried out in the Elutrap apparatus (S&S) in TBE. The DNA fragments isolated are then inserted into pEX plasmids.

Plasmid preparation is carried out following the procedure in Maniatis (1982), incorporated herein by reference. After growing a bacterial clone overnight, 1.5 ml of the culture is placed in an Eppendorf tube, centrifuged for 1 min, and the supernatant removed by aspiration. The pellet is resuspended in 100 µl of an ice-cold solution of 50 mM glucose, 10 mM EDTA, 25 mM Tris (ph 8.0), and 4 mg/ml lysozyme, and incubated at 22° C. for 20 min, followed by addition of 200 µl of ice-cold 0.2M NaOH and 1% SDS. Following incubation on ice for 5 min., 150 µl of 3M potassium acetate (pH 4.8) is added. The solution is incubated on ice for 5 min, followed by centrifugation and transfer of the supernatant to a fresh tube. 600 µl phenol:chloroform:isamylalcohol (25:24:1) is added and the solution mixed and centrifuged, saving the supernatant. Two volumes of cold ethanol is then added to the supernatant, and the solution mixed and incubated at 22° C. for 2 min. The supernatant is removed and the pellet dried by inverting the tube. The pellet is washed in 70% EtOH, mixed, centrifuged, and the pellet again drained. 50 µl of TE (pH 8.0) containing 20 µg/ml DNase-free pancreatic RNase is added, mixed briefly and an aliquot removed for digestion by EcoRl. Analysis of the digestion is carried out by agarose gel electrophoresis.

The plasmid is linearized with EcoRI (ProMega SioTech) under conditions specified by the manufacturer. 200 ng of linearized plasmid DNA is added to a 3-fold molar excess of cDNA isolated as described above. The DNA is precipitated with EtOH and resuspended in 8 µl of TE (pH 8.0). One µl of 10× ligation 66 mM Tris-Cl (pH 7.6), 6.6 mM MgCl$_2$, 10 mM dithiotheitol, 66 mM ATP) buffer is added, followed by addition of 10 units of T4 DNA ligase. The mixture is incubated at 12° C. for 8 hours. A one µl aliquot is analyzed by agarose gel for ligation. 2.4 µl are used to transform bacteria by the CaCl$_2$ technique.

Colonies carrying the recombinant plasmid are identified by screening bacteria with available polyclonal antisera. Transformed cells are grown for 20 hours at 30° C. Nitrocellulose is overlayed and the filter removed and placed colony side up under 2 layers of 3 MM filter paper presoaked in LB media containing 100 µg Amp/ml. Transcription of the hybrid protein is started by incubation at 42° C. for 2 hours. The filter will be washed 3× for 30 min each in TBS and blocked in TBS supplemented with 2% dry milk overnight. The filter is then probed with affinity purified antibody. Amplication of positive colonies is carried out by incubation at 32° C. Expression of ZP proteins is induced by transfer to 42° C. for 2 hours, at which time, the recombinant ZP protein accounts for about 25% of the total SDS extracted protein. The expressed hybrid ZP protein is insoluble and is then easily purified by conventional chromatographic methods.

Alternatively, recombinant ZP DNA can be inserted into yeasts. The methylatrophic yeast such as *Pichia pastoris* can be used for efficient and large scale expression of genetically engineered proteins. M. Bluestone and P. Savage, *Chemical Week*, McGraw-Hill, Inc. (1986). These yeast utilize methanol as a base brew which the yeast metabolizes into formaldehyde with the help of an alcohol oxidase enzyme. A second enzyme will then convert the formaldehyde into dihydroxyacetone, for the next stage of yeast cell synthesis. The cDNA can be inserted in place of the gene that makes the alcohol oxidase so that recombinant DNA from the ZP protein can be substituted at the site where the alcohol oxidase gene would normally be. Because this site would be modified in yeast would still respond to methanol only therefore switching to ethanol or to a carbohydrate food source would cause expression or non-expression of the inserted gene. The expression of the lacZ gene from two methanol-regulated promoters can now be carried out in *Pichia pastoris* as described by Tschopp et al., *Nucleic Acids Research* 15(9):3859 (1987).

EXAMPLE 5

PURIFICATION OF RECOMBINANT ZONA PELLUCIDA PROTEIN

Recombinant ZP protein is expressed as described in Example 4.

Figure 6:
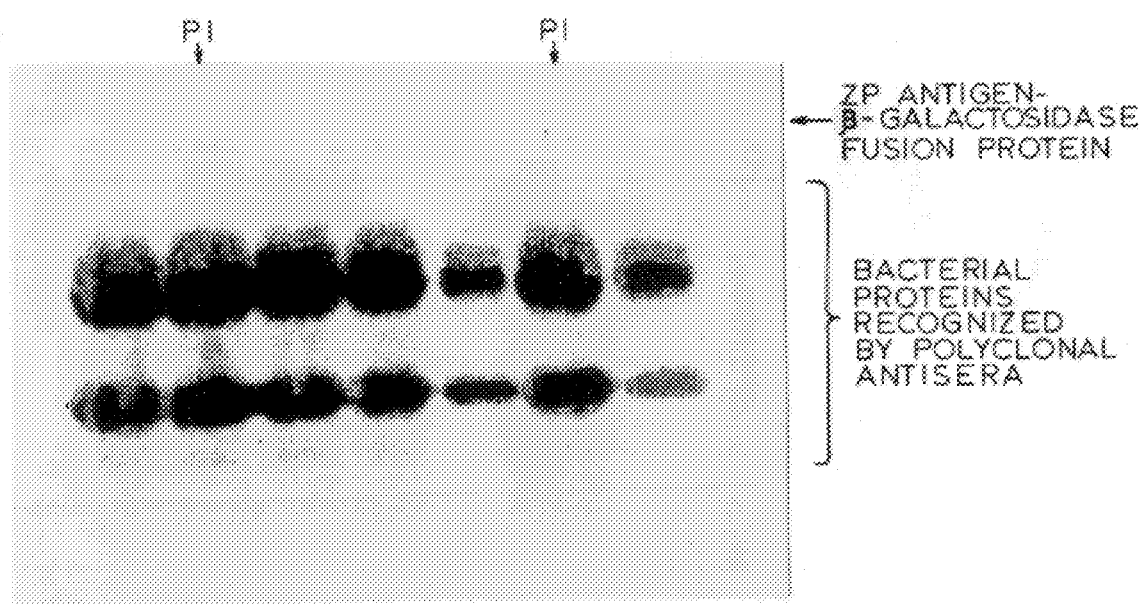
FIG. 6 demonstrates SDS-PAGE Immunoblot of λgt11DNA from clone P1.

The λgt 11 recombinant lysogen was used to infect *E. coli* Y1089. The *E. coli* was grown in LB medium supplemented with 0.2% maltose at 32° C. to an optical density (600 nm) of 0.5. The culture was then shifted to 42° C. and incubated for an additional 20 minutes. At the end of this time IPTG was added to derepress the lac repressor so that the lacZ-directed gene containing the recombinant is expressed. The cells were incubated at 37°–38° for 60 minutes and cells were frozen in liquid nitrogen and thawed to lyse the cells. The lysate was collected in 0.1M Tris buffer (ph 7.5) and passed over a Sephacel column and the void volume containing protein having molecular weights greater than 100 Kd was collected. Since the expressed protein will be a fused to β-galactosidase protein in this case, this is a rapid way to partially purify this protein. This protein fraction is then analyzed by SDS-PAGE and immunoblotting to detect the expressed antigen. FIG. 6 shows a SDS-PAGE immunoblot of a ZP antigen-fusion protein expressed by the P1 clone. The nitrocellulose transfer was probed with rabbit anti-HSPZ. Multiple low molecular weight bacterial proteins are recognized in all control samples, but the two lanes with the P1 insert show expression of a ZP specific fusion protein.

Protein will be isolated from the pEX plasmids by extracting the protein from the bacteria. Because the recombinant cro-β-galactosidase hybrid protein accounts for about 25% of sodium dodecyl sulfate extracted protein, it can be precipitated and run over Sephacel and ion exchange columns or with preparative electrophoresis to purify the protein sufficiently to purify for immunization of animals. The recombinant protein isolated from the yeast culture media could also be purified by these methods.

EXAMPLE 6

IMMUNIZATION WITH Zona pellucida

Active immunization with zona pellucida protein has been shown to be effective in inhibiting fertilization in animals. Active immunization of rabbits also results in the impairment of ovarian follicular development and therefore steroid hormone production in rabbits. (FIGS. 7A–7F).

ZP protein (300 µg/0.5 ml; 0.1M PBS) is emulsified in 0.5 ml Complete Freund's adjuvant (CFA). Half of the dose is administered intradermally in multiple sites, and half was injected subscapularly. Control animals are injected with an emulsion consisting of 0.5 ml CFA emulsified with 0.5 ml PBS. The animals receive a boost immunization 4 weeks after the primary injection. This boost included a preparation identical to the initial one except that Freund's Incomplete Adjuvant is used. In order to evaluate ovarian function, animals are treated with hCG, and serum progesterone levels were determined. Some animals of each group were killed at least 12 hours after hCG administration, and ovaries were weighed and examined for ovulation sites. Alternatively, animals received porcine FSH (Reheis Chemical Co., Phoenix, Ariz. 0.5 mg/animal twice daily for 3 days) before hCG to induce superovulation. The results of these studies show that ovarian function is altered as evidenced by lack of follicle cell differentiation and steroid production. (See FIGS. 7A–7F). Serum progesterone levels were determined in rabbits immunized with porcine ZP. Responses of animals given 50 IU hCG were determined by RIA of progesterone levels. Serum samples tested were taken periodically during the 21-day period in which pseudopregnancy normally follows such hCG treatment. Each histogram represents the mean ±S.D. of serum progesteron concentration (nanograms of progesterone per ml serum). FIGS.7A and 7D show progesterone profiles of control (adjuvant only) and experimented (ZP-immunized) animals, respectively, before immunization. FIGS.7B and 7E show similar determination made 20 weeks after primary immunization. FIGS. 7C and 7F show progesterone profiles of nonboosted animals only after FSH/hCG treatment 28 weeks after primary immunization. The use of the monoclonal antibodies R5 and R7 for passive immunization can also result in reduced fertility levels in rabbits. The monoclonal antibody designated PSI is made against a silver stained pig ZP protein purified by 2D-PAGE.

Figure 8:
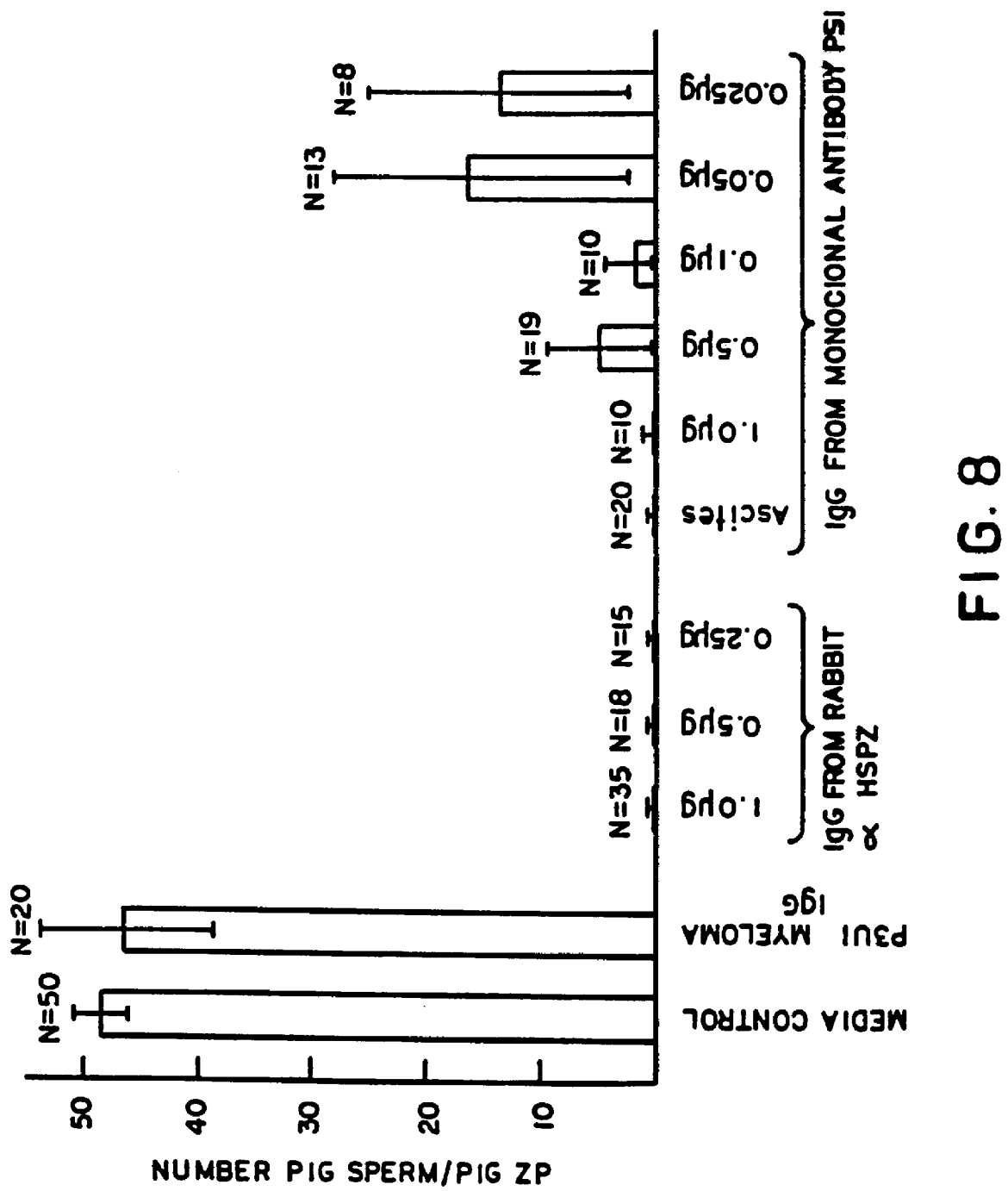
FIG. 8 demonstrates that monoclonal antibody PSI inhibits sperm binding to the ZP.

This monoclonal antibody inhibits the attachment of pig sperm to pig ZP in vitro (FIG. 8).

EXAMPLE 7

PREPARATION OF ANTI-ZONA PELLUCIDA MONOCLONAL ANTIBODIES

The procedure for preparing a hybrid cell line which produces anti-zona pellucida monoclonal antibodies involves fusion of myeloma cells of a BALB/c mouse with the spleen cells of BALB/c mice primed with zona pellucida protein. The procedure is also applicable using myeloma cells and anti-zona pellucida antibody producing cells from other sources such as humans, dogs or cats.

A. PREPARATION OF SPLEEN CELLS FOR FUSION

The zona pellucida proteins was purified as the heat solubilized total matrix from ovaries or from separation by high resolution 2D-PAGE. The zona pellucida antigen was about 95% pure (heat solubilized ZP) or 100% pure (2D-PAGE analysis) based on 2D-PAGE and silver stain analysis. The zona pellucida antigen was used to immunize adult BALB/c or C57B46 male mice by subcutaneous administration of about 30 ug emulsified in Freund's complete adjuvant. The mouse was reimmunized 2 weeks later with a further 30 ug of the protein in incomplete adjuvant given subcutaneously. After an additional 2–6 weeks, 20–40 ug of the protein were administered intravenously, and 2–4 days later the mice were sacrificed and a spleen cell suspension was prepared in the manner taught by Gefter, et al., *Somatic Cell Genetics* 3:231, 1977. Red blood cells were lysed for incubation of 15 minutes at 40° C. in $NH_4Cl$ (0.83%). The resulting cell suspension was washes by centrifugation (800×g) through heat-inactivated calf serum followed by centrifugation in protein-free medium (RRMI 1640, buffered with 7.5 mM HEPES, ph 7.2).

B. PREPARATION OF MYELOMA CELLS FOR FUSION

Myeloma cells derived from the P3U1 line and deficient in HPRT (E.C.2.4.2.8) as described by Yelton, et al., *Curr. Top. Microbiol. Immunal.* 81:1–7 (1978), were maintained in Eagle's minimum essential medium (MEM) containing 10% fetal calf and 15% horse serum. The growth of myeloma cells is inhibited by selective hypoxanthine-aminopeterin-thymidine (HAT) medium.

C. PRODUCTION OF HYBRIDS

Production of hybrids was accomplished by mixing $10^7$ BALB/c myeloma cells with $10^8$ spleen cells obtained from the zona pellucida immunized BALB/c or C57 B1/6 mice. The cell mixture was centrifuged at 800×g and the cells were resuspended for fusion in a 50% solution (w/v) of polyethylene glycol (PEG 1000) diluted in minimum essential medium (MEM) without serum following the procedure described by Gefter et al. (1977). The resulting hybridoma cells were cloned in hypoxanthine-aminopeterin-thymidine (HAT) medium by limiting dilution as described by Galfre and Milstein *Meth. Enzymol.* 73:3, 1975. Two hybridoma cell lines R5 and PSI have been selected because the cell line R5 produces an antibody which recognizes the protein portion of ZP antigens of multiple animal species. The antibody PSI appears to recognize a carbohydrate determinant on multiple species of ZP and this antibody also inhibits sperm from binding to the surface of the ZP. (FIG. 8).

The hybridoma cell lines designated R5 and PSI were deposited with the American Type Culture Collection (ATCC), Rockville, Md., U.S.A., Deposit Accession Nos. HB9565, and HB9566, respectively, on Oct. 8, 1987. The deposits are available pursuant to the patent laws and regulations of the United States and of those countries foreign to the United States in which counterparts of this application are filed. The availability of a deposit does not constitute a license to practice the invention of this application in derogation of any patent issued thereon or on any division or continuation of this application.

D. TESTING OF THE CLONES FOR PRODUCTION OF ANTI-ZONA PELLUCIDA ANTIBODY

Linbro (Flow Lab) microtiter 96 well plates were coated with 50–100 ug of total rabbit or pig ZP protein and incubated at 20° C. overnight. After washing the wells three times with 0.1M Tris (pH 7.5)—1% nonidet P-40, containing 5% Carnation Instant Milk and 0.085 sodium azide, 0.05 ml of the culture supernatants were added and incubated at 40° C. overnight. The supernatant was removed after washing three times with RIA buffer and the antibodies were detected using the Hybridoma Screening Kit (Bethesda Research Labs). Controls for non-specific binding were included by omitting either the second antibody or the culture supernatant.

The hybridoma cells designated R2, R5, R7, and PSI were grown as an ascites form by intraperitoneal injection into pristane-treated mice (Galfre and Milstein, *Meth. Enzymol.* 73 (part B) 1 (1981)), and the resulting ascites fluid was used as a source of the monoclonal antibody for immunoblots and biological assays.

---

I claim:

1. A pharmaceutical composition useful for inducing the production in an individual of antibodies to zona pellucida comprising a pharmaceutically acceptable carrier and an immunogenically effective amount of a non-naturally occurring non-rodent zona pellucida polypeptide encoded by a nucleic acid selected from the group consisting of the nucleic acids set out in SEQ ID NO: 3 and SEQ ID NO: 4 and nucleic acids encoding polypeptides having immunological cross-reactivity with zona pellucida proteins encoded by the nucleic acids set out in SEQ ID NO: 3 or SEQ ID NO: 4; and wherein said zona pellucida polypeptide is produced in a host cell from a species different from the species from which the nucleic acid is derived.

2. The pharmaceutical composition of claim 1 further comprising an adjuvant.

3. A contraceptive composition comprising a contraceptively effective amount of a non-naturally occurring non-rodent zona pellucida polypeptide and a pharmaceutically acceptable carrier, said non-naturally occurring non-rodent zona pellucida polypeptide selected from the group consisting of zona pellucida polypeptides encoded by the nucleic acids set out in SEQ ID NO: 3 and SEQ ID NO: 4 and nucleic acids encoding polypeptides having immunological cross-reactivity with proteins encoded by the nucleic acid set out in SEQ ID NO: 3 or SEQ ID NO: 4, and wherein said zona pellucida polypeptides are produced in a host cell from a species different from which the nucleic acid is derived.

4. The contraceptive composition of claim 3 further comprising an adjuvant.

5. A non-naturally occurring non-rodent zona pellucida polypeptide comprising the expression product of a nucleic acid selected from the group consisting of the nucleic acids set out in SEQ ID NO: 3 and SEQ ID NO: 4 and nucleic acids encoding an expression product having immunological cross-reactivity with an expression product encoded by a nucleic acid set out in SEQ ID NO: 3 or SEQ ID NO: 4; and wherein said expression products are produced in a host cell from a species different from the species from which said nucleic acid is derived.

6. A non-naturally occurring non-rodent zona pellucida polypeptide comprising the expression product of a nucleic acid encoding a mammalian zona pellucida polypeptide which polypeptide, when used to immunize a mammal, induces in said mammal, antibodies which bind to the immunized mammals zona pellucida and wherein said nucleic acid is selected from the group consisting of the nucleic acids set out in SEQ ID NO: 3 and SEQ ID NO: 4 and nucleic acids encoding zona pellucida polypeptides having immunological cross-reactivity with the zona pellucida polypeptides encoded by the nucleic acids set out in SEQ ID NO: 3 or SEQ ID NO: 4; and wherein said expression products are produced in a host cell from a species different from the species from which said nucleic acid is derived.

7. A method for inducing the production of antibodies in an individual to zona pellucida protein, the method comprising immunizing said individual with a non-naturally occurring non-rodent zona pellucida polypeptide, wherein said non-naturally occurring non-rodent zona pellucida polypeptide is selected from the group consisting of zona pellucida polypeptides encoded by the DNAs set out in SEQ ID NO: 3 and SEQ ID NO: 4 and polypeptides immunologically cross-reactive with the polypeptides encoded by the DNAs set out in SEQ ID NO: 3 or SEQ ID NO: 4; and wherein said zona pellucida polypeptides are produced in a host cell from a species different from which the nucleic acid is derived.

8. A contraceptive method comprising:

administering to a mammal a contraceptively effective dose of a non-naturally occurring non-rodent zona pellucida polypeptide thereby inducing in said mammal anti-zona pellucida antibodies, which antibodies bind said mammal's zona pellucida, and wherein said non-naturally occurring non-rodent zona pellucida polypeptide is selected from the group consisting of zona pellucida polypeptides encoded by the DNAs set out in SEQ ID NO: 3 and SEQ ID NO: 4 and polypeptides immunologically cross-reactive with polypeptides encoded by DNAs set out in SEQ ID NO: 3 or SEQ ID NO: 4; and wherein said zona pellucida polypeptides are produced in a host cell from a species different from which the nucleic acid is derived.

9. A contraceptive method comprising:

administering to a mammal a contraceptively effective dose of a non-naturally occurring non-rodent zona pellucida polypeptide, wherein said non-naturally occurring non-rodent zona pellucida polypeptide is selected from the group consisting of zona pellucida polypeptides encoded by the DNAs set out in SEQ ID NO: 3 and SEQ ID NO: 4, and polypeptides immunologically cross-reactive with the polypeptides encoded by the DNAs set out in SEQ ID NO: 3 or SEQ ID NO: 4; and wherein said zona pellucida polypeptides are produced in a host cell from a species different from which the nucleic acid is derived.

10. A contraceptive method comprising:

administering to a mammal a contraceptively effective dose of a pharmaceutical composition comprising a pharmaceutically acceptable carrier and an immunogenically effective amount of a non-naturally occurring non-rodent zona pellucida polypeptide encoded by a nucleic acid selected from the group consisting of the nucleic acids set out in SEQ ID NO: 3 and SEQ ID NO: 4 and nucleic acids encoding polypeptides having immunological cross-reactivity with zona pellucida proteins encoded by the nucleic acids set out in SEQ ID NO: 3 or SEQ ID NO: 4; and wherein said zona pellucida polypeptide is produced in a host cell from a species different from the species from which the nucleic acid is derived.

* * * * *